United States Patent
Dietrich et al.

(10) Patent No.: US 7,414,011 B2
(45) Date of Patent: Aug. 19, 2008

(54) PHENYLSULFONYL UREAS, PROCESS FOR THEIR PREPARATION AND THEIR USE AS HERBICIDES AND PLANT GROWTH REGULATORS

(75) Inventors: Hansjörg Dietrich, Kriftel (DE); Christian Waldraff, Frankfurt (DE); Lothar Willms, Hofheim (DE); Hermann Bieringer, Eppstein (DE); Christopher Rosinger, Hofheim (DE); Felix Thürwächter, Bad Homburg (DE); Thomas Auler, Bad Soden (DE)

(73) Assignee: Hoechst Schering Agrevo GmbH, Berlin, DE (US)

( * ) Notice: Subject to any disclaimer, the term of this patent is extended or adjusted under 35 U.S.C. 154(b) by 0 days.

(21) Appl. No.: 11/224,153

(22) Filed: Sep. 12, 2005

(65) Prior Publication Data

US 2006/0014644 A1    Jan. 19, 2006

Related U.S. Application Data

(60) Division of application No. 10/659,201, filed on Sep. 9, 2003, which is a continuation of application No. 09/499,997, filed on Feb. 8, 2000, now abandoned.

(30) Foreign Application Priority Data

Feb. 10, 1999   (DE) ............................. 199 05 453

(51) Int. Cl.
| | |
|---|---|
| C07D 239/42 | (2006.01) |
| C07D 239/46 | (2006.01) |
| C07D 239/47 | (2006.01) |
| A01N 43/54 | (2006.01) |
| A01N 43/66 | (2006.01) |
| C07D 251/42 | (2006.01) |
| C07D 251/22 | (2006.01) |
| C07D 251/26 | (2006.01) |

(52) U.S. Cl. ............ 504/239; 504/242; 504/243; 504/227; 544/320; 544/321; 544/330; 544/316; 544/318; 544/180; 544/219

(58) Field of Classification Search ............ 544/316, 544/318, 320, 321, 330; 504/239, 242, 243
See application file for complete search history.

(56) References Cited

U.S. PATENT DOCUMENTS 5,362,885 A * 11/1994 Arabori et al. .......... 548/561
5,658,854 A * 8/1997 Schnabel et al. .......... 504/214
5,849,666 A * 12/1998 Kehne et al. .......... 504/214
5,922,646 A * 7/1999 Schnabel et al. .......... 504/214

FOREIGN PATENT DOCUMENTS

| | | |
|---|---|---|
| CA | 2005595 | 7/1990 |
| DE | 39 00 472 | 7/1990 |
| DE | 42 30 933 | 3/1994 |
| DE | 43 22 067 | 1/1995 |
| EP | 0007687 | 2/1980 |
| EP | 0030138 | 6/1981 |
| EP | 0 116 518 | 8/1984 |
| WO | WO-94/06778 A1 * | 3/1994 |

OTHER PUBLICATIONS

Chemical Abstracts, vol. 62, No. 9, also referred to as XP002137748, 1965, 10361.
Database Caold 'Online!, Chemical Abstracts Service, Database Accession No. 56:6669B, also referred to as XP002137749, vol. 56, No. 7.
Clare BW Supuran, Part 41, Jan. 1, 1997, also referred to as XP004086654, pp. 311-319.
Mania D. et al, Jan. 1, 1983, also referred to as XP 000613953, pp. 464,469.

* cited by examiner

*Primary Examiner*—Venkataraman Balasubram
(74) *Attorney, Agent, or Firm*—Frommer Lawrence & Haug LLP

(57) ABSTRACT

Disclosed are compounds of the formula (I) or salts thereof

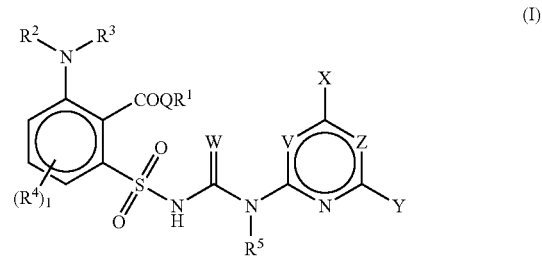

in which $R^1$, $R^2$, $R^3$, $R^4$, I, $R^5$, Q, $R^4$, W, X, Y, V and Z, are as defined in the specification, which are suitable for use as herbicides or plant growth regulators. Also disclosed are processes for preparing the compounds of formula (I) or salts thereof.

3 Claims, No Drawings

PHENYLSULFONYL UREAS, PROCESS FOR THEIR PREPARATION AND THEIR USE AS HERBICIDES AND PLANT GROWTH REGULATORS

DESCRIPTION

This application is a divisional application of U.S. Ser. No. 10/659,201, filed on 9 Sep. 2003, now allowed, which is a continuation of U.S. Ser. No. 09/499,997, filed on 8 Feb. 2000, now abandoned.

It is known that substituted phenylsulfonyl ureas have herbicidal properties. These are benzoic acid derivatives of the general formula A (EP-A-7 687 and EP-A-30 138).

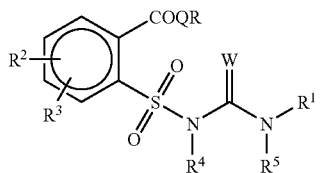

(A)

Furthermore, DEA 322.067 discloses that acylamino-substituted phenylsulfonyl ureas have herbicidal properties.

Surprisingly, specific 1,2,3-substituted phenylsulfonyl ureas have now been found which are particularly suitable for use as herbicides or plant growth regulators.

Accordingly, the present invention provides compounds of the formula, (I) or salts thereof

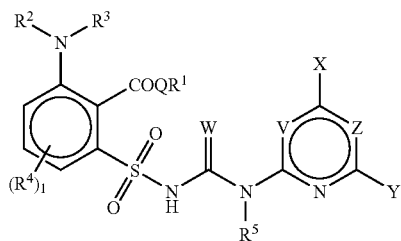

(I)

in which $R^1$ is a hydrogen atom, a hydrocarbon radical or a heterocyclyl radical, where each of the two last-mentioned radicals is unsubstituted or substituted and, including substituents, has from 1 to 30 carbon atoms, preferably from 1 to 20 carbon atoms, $R^2$ is a group of the formula $R^0$-$Q^0$- in which $R^0$ is a hydrogen atom, a hydrocarbon radical or a heterocyclyl radical, where each of the two last-mentioned radicals is unsubstituted or substituted and, including substituents, has from 1 to 30, carbon atoms, preferably from 1 to 20 carbon atoms, and $Q^0$ is a direct bond or a divalent group of the formula —O— or —N($R^\#$)—, where $R^\#$ is a hydrogen atom, an acyl radical or a hydrocarbon radical and where the last-mentioned radical is unsubstituted or substituted and, including substituents, has from 1 to 30 carbon atoms, preferably from 1 to 20 carbon atoms, $R^3$ is a hydrogen atom, a hydrocarbon radical or a heterocyclyl radical, where each of the two last-mentioned radicals is unsubstituted or substituted and, including substituents, has from 1 to 30 carbon atoms, preferably from 1 to 20 carbon atoms, $R^4$ independently of one another, are halogen, OH, SH, a nitrogen-containing radical which does not contain any carbon or a carbon-containing radical which has from 1 to 30 carbon atoms, preferably from 1 to 20 carbon atoms, is 0, 1, 2 or 3, preferably 0 or 1, $R^5$ is a hydrogen atom or a hydrocarbon radical which is unsubstituted or substituted and, including substituents, has from 1 to 20 carbon atoms, preferably from 1 to 10 carbon atoms, for example unsubstituted or substituted $(C_1$-$C_4)$alkyl, preferably H or $CH_3$, Q is O, S or NR*, $R^*$ is a hydrogen atom or a $C_1$-$C_{10}$-hydrocarbon radical which is unsubstituted or substituted and, including substituents, has from 1 to 20 carbon atoms, preferably from 1 to 10 carbon atoms, for example $(C_1$-$C_4)$alkyl, $(C_3$-$C_4)$alkenyl or $(C_3$-$C_4)$alkynyl, where each of the three last-mentioned radicals is unsubstituted or substituted by one or more radicals selected from the group consisting of halogen, $(C_1$-$C_4)$alkoxy and $(C_1$-$C_4)$alkylthio, W is an oxygen or sulfur atom, X,Y independently of one another are a hydrogen atom, halogen, $(C_1$-$C_4)$alkyl, $(C_1$-$C_4)$alkoxy, $(C_1$-$C_4)$alkylthio, where each of the 3 last-mentioned radicals is unsubstituted or substituted by one or more radicals selected from the group consisting of halogen, $(C_1$-$C_4)$alkoxy and $(C_1$-$C_4)$alkylthio, or are mono- or di[$(C_1$-$C_4)$alkyl]amino, $(C_2$-$C_6)$alkenyl, $(C_2$-$C_6)$alkynyl, $(C_3$-$C_6)$alkenyloxy or $(C_3$-$C_6)$alkynyloxy, and V, Z independently of one another are CH or N.

The compounds of the formula (I) can form salts where the hydrogen of the —$SO_2$—NH— group is replaced by an agriculturally suitable cation. These salts are, for example, metal salts, in particular alkali metal salts or alkaline-earth metal salts, in particular sodium salts and potassium salts, or else ammonium salts or salts with organic amines. Likewise, salt formation can be carried out by adding an acid to basic groups, such as, for example, amino and alkylamino. Suitable acids for this purpose are strong inorganic and organic acids, for example HCl, HBr, $H_2SO_4$ or $HNO_3$.

In the formula (I), the two radicals $R^0$ and $R^\#$, $R^2$ and $R^3$ and $R^*$ and $R^1$ together can in each case form a nitrogen-containing heterocyclic ring.

Carbon-containing radicals are organic radical containing at least one carbon atom, preferably from 1 to 30 carbon atoms, particularly preferably from 1 to 20 carbon atoms, and furthermore at least one atom of one or more other elements of the Periodic Table of the Elements, such as H, Si, N, P, S, F, Cl, Br or I. Examples of carbon-containing radicals are unsubstituted or substituted hydrocarbon radicals, which can be attached to the skeleton directly or via a heteroatom such as N, S, P or O, unsubstituted or substituted heterocyclyl radicals, carbon-containing acyl radicals or cyano.

In the formula (I) and all the formulae below, the carbon-containing radicals, such as alkyl alkoxy, haloalkyl, haloalkoxy, alkylamino and alkylthio, and the corresponding unsaturated and/or substituted radicals, can in each case be straight-chain or branched in the carbon skeleton. Unless specifically stated otherwise, the lower carbon skeletons, for example those having 1 to 6 carbon atoms, or in the case of unsaturated groups those having 2 to 6 carbon atoms, are preferred for these radicals. Alkyl radicals, also in the composed meanings such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the unsaturated radicals which are possible and which correspond to the alkyl radicals; alkenyl denotes, for example, allyl, 1-methylprop-2-en-1-yl, 2-methylprop-2-en-1-yl, but-2-en-1-yl, but-3-en-1-yl, 1-methylbut-3-en-1-yl; and 1-methylbut-2-en-1-yl; alkynyl is, for example, propargyl, but-2-yn-1-yl, but-3-yn-1-yl, 1-methylbut-3-yn-1-yl.

Alkenyl in the form $(C_3-C_4)$alkenyl, $(C_3-C_5)$alkenyl, $(C_3-C_6)$alkenyl, $(C_3-C_8)$alkenyl or $(C_3-C_{12})$alkenyl is preferably an alkenyl radical having 3 to 4, 3 to 5, 3 to 6, 3 to 8 and 3 to 6 carbon atoms, respectively, where the double bond is not located at the carbon atom which is linked to the remainder of the molecule of the compound (I) ("yl" position). This applies correspondingly to $(C_3-C_4)$alkynyl etc., $(C_3-C_4)$alkenyloxy etc. and $(C_3-C_4)$alkynyloxy etc.

Cycloalkyl is a carbocyclic saturated ring system having 3-8 carbon atoms, for example cyclopropyl, cyclobutyl, cyclopentyl or cyclohexyl.

Nitrogen-containing radicals which do not contain any carbon are radicals which preferably contain from 1 to 10 nitrogen atoms, particularly preferably 1 or 2 nitrogen atoms, and furthermore preferably one or more atoms of one or more elements of the Periodic Table of the Elements which are different from carbon, such as H, O or S. Examples of nitrogen-containing radicals which do not contain any carbon are $NH_2$, $NO_2$, NHOH, NO, $NH-NH_2$ or $N_3$.

Halogen is, for example, fluorine, chlorine, bromine or iodine. Haloalkyl, -alkenyl and -alkynyl are alkyl, alkenyl or alkynyl which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

A hydrocarbon radical has a straight-chain, branched or cyclic and saturated or unsaturated aliphatic or aromatic hydrocarbon radical, for example alkyl, alkenyl, alkynyl, cycloalkyl, cycloalkenyl or aryl; aryl in this context is a mono-, bi- or polycyclic aromatic system, for example phenyl, naphthyl, tetrahydronaphthyl, indenyl, indanyl, pentalenyl, fluorenyl and the like, preferably phenyl;

a hydrocarbon radical is preferably alkyl, alkenyl or alkynyl having up to 12 carbon atoms or cycloalkyl having 3, 4, 5, 6 or 7 ring atoms or phenyl.

A heterocyclic radical or ring (heterocyclyl) can be saturated, unsaturated or heteroaromatic and substituted or unsubstituted; preferably, it contains one or more heteroatoms in the ring, preferably selected from the group consisting of N, O and S; it is preferably an aliphatic heterocyclyl radical having 3 to 7 ring atoms or a heteroaromatic radical having 5 or 6 ring atoms and contains 1, 2 or 3 heteroatoms. The heterocyclic radical can be, for example, a heteroaromatic radical or ring (heteroaryl), such as, for example, a mono-, bi- or polycyclic aromatic system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or it is a partially or fully hydrogenated radical, such as oxiranyl, oxetanyl, pyrrolidyl, piperidyl, piperazinyl, dioxolanyl, morpholinyl, tetrahydrofuryl. Substituents which are suitable for a substituted heterocyclic radical are the substituents mentioned further below, and additionally also oxo. The oxo group can also be present on the hetero ring atoms which may exist at various oxidation levels, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl are, for example, a substituted radical which is derived from the unsubstituted skeleton, the substituents being, for example, one or more, preferably 1, 2 or 3, radicals selected from the group-consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and also unsaturated aliphatic radicals which correspond to the above-mentioned saturated hydrocarbon-containing radicals, such as alkenyl, alkynyl, alkenyloxy, alkynyloxy, etc. Preferred among radicals having carbon atoms are those having 1 to 4 carbon atoms, in particular 1 or 2 carbon atoms. Preferred are, in general, substituents selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Especially preferred in this context are the substituents methyl, methoxy and chlorine.

Phenyl which may be substituted is preferably phenyl which is unsubstituted or mono- or polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Mono- or disubstituted amino is a chemically stable radical selected from the group consisting of the substituted amino radicals, which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred in this context are alkyl radicals having 1 to 4 carbon atoms; aryl is in this context preferably phenyl or substituted phenyl; acyl is as defined further below, preferably formyl, $(C_1-C_4)$alkylcarbonyl or $(C_1-C_4)$alkylsulfonyl. This applies correspondingly to substituted hydroxylamino or hydrazino.

An acyl radical is the radical of an organic acid which is formed formally by eliminating an OH group from the organic acid, for example the radical of a carboxylic acid and radicals of acids derived therefrom, such as thiocarboxylic acid, unsubstituted or N-substituted iminocarboxylic acids or the radicals of carbonic monoesters, unsubstituted or N-substituted carbamic acids, sulfonic acids, sulfinic acids, phosphonic acids and phosphinic acids.

A preferred acyl radical is formyl or aliphatic acyl selected from the group consisting of $CO-R^x$, $CS-R^x$, $CO-OR^x$, $CS-OR^x$, $CS-SR^x$, $SOR^Y$ or $SO_2R^Y$, where $R^x$ and $R^Y$ are in each case a $C_1-C_{10}$-hydrocarbon radical which is unsubstituted or substituted, or aminocarbonyl or aminosulfonyl, where the two last-mentioned radicals are unsubstituted, N-monosubstituted or N,N-disubstituted.

Acyl is, for example, formyl, haloalkylcarbonyl, alkylcarbonyl such as $(C_1-C_4)$alkylcarbonyl, phenylcarbonyl, where the phenyl ring may be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also provides all stereoisomers embraced by formula (I) and mixtures of these. Such compounds of the formula (I) contain one or more asymetric carbon atoms or else double bonds which are not mentioned separately in the formula (I). Formula (I) embraces all possible stereoisomers which are defined by their specific spatial form, such as enantiomers, diastereomers and Z and E isomers, they can be obtained by customary methods from mixtures of the stereoisomers or be prepared by stereoselective reactions in combination with the use of stereochemically pure starting materials.

The abovementioned examples of radicals or ranges of radicals which come under the general terms such as "alkyl", "acyl", "substituted radicals", etc., are not meant to be complete lists. The general terms also include the definitions of ranges of radicals in groups of preferred compounds given further below, in particular ranges of radicals which include specific radicals from the examples in the tables.

Compounds of the formula (I) according to the invention or their salts which are of particular interest, mainly for reasons of higher herbicidal activity, better selectivity and/or because they can be prepared more easily are those in which $R^1$ is H, $(C_1-C_6)$alkyl, $(C_3-C_6)$alkenyl, $(C_3-C_6)$alkynyl, where each of the three last-mentioned radicals is unsubstituted or substituted by one or more radicals selected from the group consisting of halogen, unsubstituted and substituted phenyl, unsubstituted and substituted heterocyclyl having 3 to 6 ring atoms, unsubstituted and substituted $(C_3-C_6)$cycloalkyl, $(C_1-C_4)$alkoxy, $(C_1-C_4)$alkylthio, $[(C_1-C_4)$alkoxy]carbonyl and $[(C_1-C_4)$haloalkoxy]carbonyl, or is unsubstituted or substituted $(C_3-C_6)$cycloalkyl, substituted or unsubstituted $(C_3-C_6)$cycloalkenyl, unsubstituted or substituted phenyl, unsubstituted or substituted heterocyclyl having 3 to 6 ring atoms, where substituted phenyl, substituted heterocyclyl, substituted cycloalkyl or substituted cycloalkenyl carry, as substituents, one or more radicals selected from the group consisting of halogen, $(C_1-C_4)$alkyl, $(C_1-C_4)$haloalkyl, $(C_1-C_4)$alkoxy, $(C_1-C_4)$alkyl, $di[(C_1-C_4)$alkoxy]$(C_1-C_4)$alkyl, $(C_1-C_4)$haloalkoxy, $(C_1-C_4)$alkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $NR^8R^9$, $[(C_1-C_4)$alkoxy]carbonyl, $[(C_1-C_4)$haloalkoxy]carbonyl, $[(C_1-C_4)$alkyl]carbonyl, OH, phenyl, CN and $NO_2$ and $R^2$ is a group of the formula $R^0-Q^0$, in which $R^0$ is a hydrogen atom, $(C_1-C_{12})$alkyl, $(C_2-C_{12})$alkenyl or $(C_2-C_{12})$alkynyl, where each the three last-mentioned radicals is unsubstituted or substituted by one or more radicals selected from the group consisting of halogen, $(C_1-C_6)$alkoxy, $(C_1-C_6)$haloalkoxy, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, $[(C_1-C_6)$alkoxy]carbonyl, $[(C_1-C_6)$haloalkoxy]carbonyl, $CONR^6R^7$, $SO_2NR^6R^7$, CN, OH, SH, $(C_3-C_6)$cycloalkyl, $NR^8R^9$, unsubstituted or substituted phenyl, unsubstituted or substituted heterocyclyl, or is $(C_3-C_6)$cycloalkyl, $(C_3-C_6)$cycloalkenyl, phenyl or heterocyclyl, preferably having 3 to 6 ring atoms, where the four last-mentioned radicals may be unsubstituted or substituted, and in which $Q^0$ is a direct bond or a divalent group of the formula —O— or —N($R^\#$)— where $R^\#$ is a hydrogen atom, an acyl radical or $(C_1-C_{12})$alkyl, $(C_2-C_{12})$alkenyl or $(C_2-C_{12})$alkynyl, where each of the 3 last-mentioned radicals is unsubstituted or substituted by one or more radicals selected from the group consisting of halogen, $(C_1-C_6)$alkoxy, $(C_1-C_6)$haloalkoxy, $(C_1-C_6)$alkylthio, $(C_1-C_6)$haloalkylthio, CN, OH, $(C_3-C_6)$cycloalkyl, unsubstituted or substituted phenyl, unsubstituted or substituted heterocyclyl, or is unsubstituted or substituted $(C_3-C_6)$cycloalkyl, unsubstituted or substituted $(C_3-C_6)$cycloalkenyl or unsubstituted or substituted phenyl, and $R^0$ and $R^\#$ together with the nitrogen atom of the $NR^\#R^0$ group may form a heterocyclyl radical, preferably having 3 to 6 ring atoms, which is unsubstituted or substituted, preferably by one or more radicals selected from the group consisting of halogen, $(C_1-C_6)$alkyl, $(C_1-C_6)$alkoxy, $[(C_1-C_6)$alkoxy]carbonyl, $(C_1-C_6)$haloalkyl and oxo, $R^3$ is a hydrogen atom, $(C_1-C_{12})$alkyl, $(C_2-C_{12})$alkenyl or $(C_2-C_2)$alkynyl, where each of the 3 last-mentioned radicals is unsubstituted or substituted by one or more radicals selected from the group consisting of halogen, $(C_1-C_6)$alkoxy, $(C_1-C_6)$haloalkoxy, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, $[(C_1-C_6)$alkoxy]carbonyl, $[(C_1-C_6)$haloalkoxy]carbonyl, $CONR^6R^7$, $SO_2NR^6R^7$, CN, OH, $(C_3-C_6)$cycloalkyl, $NR^8R^9$, unsubstituted or substituted phenyl, unsubstituted or substituted heterocyclyl, or is unsubstituted or substituted $(C_3-C_6)$cycloalkyl; unsubstituted or substituted $(C_3-C_6)$cycloalkenyl, unsubstituted or substituted heterocyclyl, preferably having 3 to 6 ring atoms, or unsubstituted or substituted phenyl, and $R^2$ and $R^3$ together with the nitrogen atom of the $NR^2R^3$ group $(N^1)$ may form a heterocyclyl radical, preferably having, 3 to 6 ring atoms, which is unsubstituted or substituted, preferably by one or more radicals selected from the group consisting of halogen, $(C_1-C_6)$alkyl, $(C_1-C_6)$alkoxy, $[(C_1-C_6)$alkoxy]carbonyl, $(C_1-C_6)$haloalkyl and oxo, where the oxo radical is preferably not adjacent to the nitrogen atom $(N^1)$, and $R^4$ independently of one another are halogen, CN, $(C_1-C_4)$alkyl, $(C_1-C_4)$alkoxy, $(C_2-C_6)$alkenyl, $(C_2-C_6)$alkynyl, $(C_3-C_6)$alkenyloxy, $(C_3-C_6)$alkynyloxy, where each of the 6 last-mentioned radicals is unsubstituted or substituted by one or more radicals selected from the group consisting of halogen, $(C_1-C_6)$alkoxy, $(C_1-C_6)$haloalkoxy, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, $[(C_1-C_6)$alkoxy]carbonyl, $[(C_1-C_6)$haloalkoxy]carbonyl; $CONR^6R^7$, $SO_2NR^6R^7$, CN, OH, $(C_3-C_6)$cycloalkyl, $NR^8R^9$, unsubstituted or substituted phenyl or unsubstituted or substituted heterocyclyl, or is unsubstituted or substituted $(C_3-C_6)$cycloalkyl, unsubstituted or substituted $(C_3-C_6)$cycloalkenyl, unsubstituted or substituted heterocyclyl, preferably having 3 to 6 ring atoms, unsubstituted or substituted phenyl, $[(C_1-C_4)$alkyl]carbonyl or $[(C_1-C_4)$alkoxy]carbonyl, where each of the two last-mentioned radicals is unsubstituted or substituted in the alkyl moiety by one or more halogen atoms, or is a radical of the formula C(O)—NR'—R", C(S)—NR'—R", CR'=N-Q$^1$-R", $S(O)_m$-Q$^1$-R"', $P(O)_n$(-Q$^1$-R"'Q$^2$-R"), NR'-Q$^1$-R" or NR'''—N=CR'—R", where R', R" and R''' independently of one another are a hydrogen atom, an acyl radical or an unsubstituted or substituted $(C_1-C_{10})$hydrocarbon radical, R"" is a carbon-containing acyl radical or an unsubstituted or substituted $(C_1-C_{10})$hydrocarbon radical, and Q$^1$ and Q$^2$ independently of one another are a direct bond or a divalent group of the formula —O— or —N(R$^+$)—, where R$^+$ is a hydrogen atom, an acyl radical, or an unsubstituted or substituted $(C_1-C_{10})$hydrocarbon radical, and m=0, 1, 2 or 3, and n=0, 1 or 2, and R' together with R", R⁺ together with R', R⁺ together with R" or R⁺ together with R"" may in each case form a heterocyclyl radical, preferably having 3 to 6 ring atoms,
  which is unsubstituted or substituted, preferably by one or more radicals selected from the group consisting of halogen, $(C_1-C_6)$alkyl, $(C_1-C_6)$alkoxy, $[(C_1-C_6)$alkoxy]carbonyl, $(C_1-C_6)$haloalkyl and oxo,
l is 0, 1 or 2, preferably 0 or 1,
$R^5$ is H or $(C_1-C_4)$alkyl which is unsubstituted or substituted,
$R^6$ and $R^7$ independently of one another are H, $(C_1-C_6)$alkyl, $(C_3-C_6)$alkenyl, $(C_3-C_6)$alkynyl, unsubstituted or substituted phenyl or unsubstituted or substituted heterocyclyl or
  $R^6$ and $R^7$ together with the nitrogen atom of the $NR^6R^7$ group may form a heterocyclyl radical having 5 or 6 ring atoms which may optionally contain one or more additional heteroatoms selected from the group consisting of N, O and S and which is unsubstituted or mono- or polysubstituted by radicals selected from the group consisting of $(C_1-C_4)$alkyl and oxo, and
$R^8$ and $R^9$ independently of one another are $(C_1-C_4)$alkylcarbonyl, $(C_1-C_4)$haloalkylcarbonyl, $(C_1-C_4)$alkoxycarbonyl or $(C_1-C_4)$alkylsulfonyl or together with the nitrogen atom of the $NR^8R^9$ group may form a heterocyclyl radical having 5 or 6 ring atoms which may optionally contain one or more additional heteroatoms selected from the group consisting of N, O and S and which is unsubstituted or mono- or polysubstituted by radicals selected from the group consisting of $(C_1-C_4)$alkyl and oxo, and
Q is O, S or NR*,
R* is $(C_1-C_4)$alkyl, $(C_3-C_4)$alkenyl or $(C_3-C_4)$alkynyl, where each of the three last-mentioned radicals is unsubstituted or substituted by one or more radicals selected from the group consisting of halogen, $(C_1-C_4)$alkoxy and $(C_1-C_4)$alkylthio, and
  R* and $R^1$ together with the nitrogen atom of the $NR^*R^1$ group may form a heterocyclyl radical which is unsubstituted or substituted, preferably by one or more radicals selected from the group consisting of halogen, $(C_1-C_6)$alkyl, $(C_1-C_6)$alkoxy, $[(C_1-C_6)$alkoxy]carbonyl, $(C_1-C_6)$haloalkyl and oxo,
X, Y independently of one another are H, halogen, $(C_1-C_4)$alkyl, $(C_1-C_4)$alkoxy, $(C_1-C_4)$alkylthio, where each of the three last-mentioned radicals is unsubstituted or substituted by one or more radicals from the group consisting of halogen, $(C_1-C_4)$alkoxy and $(C_1-C_4)$alkylthio, are mono- or di[$(C_1-C_4)$alkyl]amino, $(C_3-C_5)$alkenyl, $(C_3-C_5)$alkenyloxy, $(C_3-C_5)$alkynyl or $(C_3-C_5)$alkynyloxy, and where the radicals $R^1$, $R^2$, $R^3$ and $R^4$, including substituents, have up to 20 carbon atoms.

Of particular interest are compounds of the formula (I) according to the invention in which
$R^1$ is H, $(C_1-C_6)$alkyl, $(C_3-C_6)$alkenyl or $(C_3-C_6)$alkynyl, where each of the three last-mentioned radicals is unsubstituted or substituted by one or more radicals selected from the group consisting of halogen, phenyl, $(C_1-C_4)$alkoxy, $(C_1-C_4)$alkylthio, $(C_3-C_6)$cycloalkyl, heterocyclyl having 3 to 6 ring atoms and $[(C_1-C_4)$alkoxy]carbonyl, or is $(C_3-C_6)$cycloalkyl or heterocyclyl having 3 to 6 ring atoms, where each of the two last-mentioned radicals is unsubstituted; or substituted by one or more radicals selected from the group consisting of halogen, $(C_1-C_4)$alkyl and $(C_1-C_4)$alkoxy, $R^2$ is a group of the formula $R^0-Q^0-$ in which
  $R^0$ is a hydrogen atom, $(C_1-C_8)$alkyl, $(C_3-C_8)$alkenyl or $(C_3-C_8)$alkynyl, where each of the 3 last-mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $[(C_1-C_6)$alkoxy]carbonyl, $CONR^6R^7$, $SO_2NR^6R^7$, CN, OH, $(C_3-C_6)$cycloalkyl, $NR^8R^9$ and phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $NR^8R^9$, $[(C_1-C_4)$alkoxy]carbonyl, $[(C_1-C_4)$alkyl]carbonyl, phenyl, $[(C_1-C_4)$alkyl]carbonyl, CN and $NO_2$, or
  is heterocyclyl having 3 to 6 ring atoms which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $NR^8R^9$, $[(C_1-C_4)$alkoxy]carbonyl, $[(C_1-C_4)$alkyl]carbonyl, phenyl, CN and $NO_2$, or
  is $(C_3-C_6)$cycloalkyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $[(C_1-C_4)$alkoxy]carbonyl, CN, OH and phenyl, or
  is $(C_3-C_6)$cycloalkenyl which is unsubstituted or substituted by one or more radicals selected from the group consisting of halogen, $(C_1-C_4)$alkyl, $(C_1-C_4)$haloalkyl, $(C_1-C_4)$alkoxy and $[(C_1-C_4)$alkoxy]carbonyl, or
  is phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $NR^8R^9$, $[(C_1-C_4)$alkoxy]carbonyl, $[(C_1-C_4)$alkyl]carbonyl, phenyl, CN and $NO_2$, and
  $Q^0$ is a direct bond or a divalent group of the formula —O— or —NR#, in which R# is a hydrogen atom or unsubstituted or substituted $(C_1-C_4)$alkyl,
$R^3$ is a hydrogen atom, $(C_1-C_8)$alkyl, $(C_3-C_8)$alkenyl or $(C_3-C_8)$alkynyl, where each of the 3 last-mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfonyl, $(C_1-C_4)$haloalkylsulfinyl, $(C_1-C_4)$alkylsulfonyl, $(C_1-C_4)$haloalkylsulfonyl, $[(C_1-C_6)$alkoxy]carbonyl, $CONR^6R^7$, $SO_2NR^6R^7$, CN, OH, $(C_3-C_6)$cycloalkyl; $NR^8R^9$ and phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsufonyl, $NR^8R^9$, $[(C_1-C_4)$alkoxy]carbonyl, $[(C_1-C_4)$alkyl]carbonyl, phenyl, $[(C_1-C_4)$alkyl]carbonyl, CN and $NO_2$, or
  is heterocyclyl preferably having 3 to 6 ring atoms which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $NR^8R^9$, $[(C_1-C_4)$alkoxy]carbonyl, $[(C_1-C_4)$alkyl]carbonyl, phenyl, CN and $NO_2$, or
  is $(C_3-C_6)$cycloalkyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $[(C_1-C_4)$alkoxy]carbonyl, CN, OH and phenyl, or is $(C_3-C_6)$cycloalkenyl which is unsubstituted or substituted by one or more radicals selected from the group consisting of halogen; $(C_1-C_4)$alkyl, $(C_1-C_4)$haloalkyl, $(C_1-C_4)$alkoxy and $[(C_1-C_4)$alkoxy]carbonyl, or is phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $NR^8R^9$, $[(C_1-C_4)$alkoxy]carbonyl, $[(C_1-C_4)$alkyl]carbonyl, phenyl, CN and $NO_2$, and $R^2$ and $R^3$ together with the nitrogen atom $(N^1)$ may form a heterocyclyl radical of 3-6 ring atoms which may be saturated, unsaturated or heteroaromatic and may, in addition to the nitrogen atom $(N^1)$, contain one or two heteroatoms selected from the group consisting of N, O and S and which is unsubstituted or substituted by one or more radicals selected from the group consisting of $(C_1-C_6)$alkyl, preferably $(C_1-C_3)$alkyl, $(C_1-C_3)$alkoxy, halogen, $[(C_1-C_3)$alkoxy] carbonyl, $(C_1-C_3)$haloalkyl and oxo, where the oxo radical is preferably not adjacent to the nitrogen atom $(N^1)$, $R^4$ are halogen, CN, $(C_1-C_4)$alkyl, $(C_1-C_4)$alkoxy, $(C_2-C_6)$alkenyl, $(C_2-C_6)$alkynyl, $(C_3-C_6)$alkenyloxy, $(C_3-C_6)$alkynyloxy, where each of the 6 last-mentioned radicals is unsubstituted or substituted by one or more radicals selected from the group consisting of halogen, $(C_1-C_6)$alkoxy, $(C_1-C_6)$haloalkoxy, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$-haloalkylsulfinyl, $[(C_1-C_6)$alkoxy]carbonyl, $[(C_1-C_6)$haloalkoxy]carbonyl, $CONR^6R^7$, $SO_2NR^6R^7$, CN, OH, $(C_1-C_6)$cycloalkyl, $NR^8R^9$, unsubstituted or substituted phenyl, unsubstituted or substituted heterocyclyl, or are unsubstituted or substituted, $(C_3-C_6)$cycloalkyl, unsubstituted or substituted $(C_3-C_6)$cycloalkenyl, unsubstituted or substituted heterocyclyl having 3 to 6 ring atoms, unsubstituted or substituted phenyl or $[(C_1-C_4)$alkyl]carbonyl or $[(C_1-C_4)$alkoxy]carbonyl, where each of the two last-mentioned radicals is unsubstituted or substituted in the alkyl moiety by one or more halogen atoms, or are radicals of the formula $C(O)—NR'—R''$, $C(S)—NR'—R''$, $CR'=N-Q^1-R''$, $NR'-Q^1-R''$ or $NR''—N=CR'—R'''$ where R', R'' and R''' independently of one another are a hydrogen atom, an acyl radical or an unsubstituted or substituted $(C_1-C_{10})$hydrocarbon radical, and $Q^1$ and $Q^2$ independently of one another are a direct bond or a divalent group of the formula $—O—$ or $—N(R^+)—$, where $R^+$ is a hydrogen atom, an acyl radical or an unsubstituted or substituted $(C_1-C_4)$alkyl radical and R' together with R'' or $R^+$ together with R' or $R^+$ together with R'' may in each case form a heterocyclyl radical having 3 to 6 ring atoms which is, unsubstituted or substituted, preferably by one or more radicals selected from the group consisting of halogen, $(C_1-C_6)$alkyl, $(C_1-C_6)$alkoxy, $[(C_1-C_6)$alkoxy]carbonyl, $(C_1-C_6)$haloalkyl and oxo, I is 0 or 1, $R^6$ and $R^7$ independently of one another are H, $(C_1-C_4)$alkyl, $(C_3-C_4)$alkenyl, $(C_3-C_4)$alkynyl or phenyl which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$alkylthio, $(C_1-C_4)$alkylsulfonyl, $[(C_1-C_4)$alkoxy]carbonyl, CN and $NO_2$, or $R^6$ and $R^7$ together with the nitrogen atom of the $NR^6R^7$ group may form a heterocyclyl radical having 5 or 6 ring members which may contain one or more heteroatoms selected from the group consisting of N, O and S and which is unsubstituted or mono- or polysubstituted by radicals selected from the group consisting of $(C_1-C_4)$alkyl and oxo, $R^8$ and $R^9$ are $(C_1-C_4)$alkylcarbonyl, $(C_1-C_4)$haloalkylcarbonyl, $(C_1-C_4)$alkoxycarbonyl or $(C_1-C_4)$alkylsulfonyl, or together with the nitrogen atom of the $NR^8R^9$ group may form a heterocyclyl radical having 5 or 6 ring members which may contain one or more heteroatoms selected from the group consisting of N, O and S and which is unsubstituted or mono- or polysubstituted by radicals selected from the group consisting of $(C_1-C_4)$alkyl and oxo.

Also of particular interest are compounds of the formula (I) according to the invention and salts thereof in which $R^1$ is $(C_1-C_6)$alkyl which is unsubstituted or substituted by one or more radicals selected from the group consisting of halogen and $(C_1-C_4)$alkoxy, or is 3-oxetanyl, $(C_3-C_4)$alkenyl or $(C_3-C_4)$alkynyl, $R^2$ is H, $(C_1-C_6)$alkyl, $(C_3-C_6)$alkenyl, $(C_3-C_6)$alkynyl, where each of the three last-mentioned radicals is unsubstituted or substituted by one or more radicals selected from the group consisting of halogen, $(C_1-C_4)$alkoxy, $(C_1-C_4)$alkylthio, $(C_1-C_4)$alkylsulfonyl, $[(C_1-C_4)$alkoxy]carbonyl, $(C_3-C_6)$cycloalkyl, CN and OH, or is $(C_3-C_6)$cycloalkyl which is unsubstituted or substituted by one or more radicals selected from the group consisting of halogen, $(C_1-C_4)$alkyl, $(C_1-C_4)$alkoxy, $[(C_1-C_4)$alkoxy]carbonyl, CN and OH, or is $(C_3-C_6)$cycloalkenyl, $(C_1-C_4)$alkoxy, $(C_1-C_4)$alkenyloxy, $(C_1-C_4)$alkylamino or di$[(C_1-C_4)$alkyl]amino and $R^3$ is H, $(C_1-C_6)$alkyl, $(C_3-C_6)$alkenyl, $(C_3-C_6)$alkynyl, where each of the three last-mentioned radicals is unsubstituted or substituted by one or more radicals selected from the group consisting of halogen, $(C_1-C_4)$alkoxy, $(C_1-C_4)$alkylthio, $(C_1-C_4)$alkylsulfonyl, $[(C_1-C_4)$alkoxy]carbonyl, $(C_3-C_6)$cycloalkyl, CN and OH, or is $(C_3-C_6)$cycloalkyl which is unsubstituted or substituted by one or more radicals selected from the group consisting of halogen, $(C_1-C_4)$alkyl, $(C_1-C_4)$alkoxy, $[(C_1-C_4)$alkoxy]carbonyl, CN and OH, or is $(C_3-C_6)$cycloalkenyl or, $R^2$ and $R^3$ together with the nitrogen atom $(N^1)$ may form a heterocyclyl radical of 3-6, preferably 5 or 6 ring atoms which is saturated, unsaturated or heteroaromatic, which may, in addition to the nitrogen atom $(N^1)$, contain one or two heteroatoms selected from the group consisting of N, O and S and which is unsubstituted or substituted by one or more radicals selected from the group consisting of halogen, $(C_1-C_6)$alkyl, preferably $(C_1-C_3)$alkyl, $(C_1-C_3)$alkoxy, $[(C_1-C_3)$alkoxy]carbonyl and oxo, where the oxo radical is preferably not adjacent to the nitrogen atom $(N^1)$, and $R^4$ are $(C_1-C_4)$alkyl, $(C_1-C_4)$haloalkyl, $(C_1-C_4)$alkoxy or halogen, I is 0 or 1, preferably 0, $R^5$ is H or methyl, Q is O or $NR^*$, $R^*$ is H or $(C_1-C_4)$alkyl, X and Y independently of one another are $(C_1-C_4)$alkyl, $(C_1-C_4)$alkoxy, where each of the two last-mentioned radicals is unsubstituted or substituted by one or more halogen atoms, or are $(C_1-C_4)$alkylthio, halogen or mono-oder di[$(C_1-C_2)$alkyl]amino, and W is an oxygen atom.

Preferred compounds of the formula (I) according to the invention or salts thereof are those in which $R^1$ is $(C_1-C_3)$alkyl, allyl or propargyl, $R^2$ is H, $(C_1-C_4)$alkyl, $(C_3-C_5)$alkenyl, $(C_3-C_5)$alkynyl, $(C_3-C_6)$cycloalkyl or $(C_3-C_6)$cycloalkenyl, $R^3$ is H, $(C_1-C_4)$alkyl, $(C_3-C_5)$alkenyl, $(C_3-C_5)$alkynyl, $(C_3-C_6)$cycloalkyl or $(C_3-C_6)$cycloalkenyl, or $R^2$ and $R^3$ together with the nitrogen atom ($N^1$) may form a heterocyclyl radical of 3-6, preferably 5 or 6 ring atoms which is saturated, unsaturated or heteroaromatic, which may, in addition to the nitrogen atom ($N^1$), contain one or two heteroatoms selected from the group consisting of N, O and S and which is unsubstituted or substituted by one or more $(C_1-C_6)$ alkyl radicals, $R^4$ are $(C_1-C_3)$alkyl or halogen, I is 0 or 1, preferably 0, Q is O or NR*, R* is $(C_1-C_3)$alkyl, X is $(C_1-C_2)$alkyl, $(C_1-C_2)$alkoxy, $(C_1-C_2)$alkylthio, $(C_1-C_2)$haloalkyl or $(C_1-C_2)$haloalkoxy, Y is $(C_1-C_2)$alkyl, $(C_1-C_2)$alkoxy, halogen, $NHCH_3$ or $N(CH_3)_2$, V is CH or N, preferably N and Z is CH or N.

Particularly preferred compounds of the formula (I) according to the invention are salts thereof are those in which $R^1$ is $(C_1-C_3)$alkyl, allyl or propargyl and/or Q is an oxygen atom.

Particular preference is also given to compounds of the formula (I) according to the invention and salts thereof which contain a combination of radicals from the abovementioned compounds of particular interest or the preferred compounds, and also to those which contain one or more radicals from the compounds listed in Tables 1 and 2 (see below). Preference is likewise given to compounds of the formula (I) in which V=N.

The present invention also provides processes for preparing the compounds of the formula (I) according to the invention or salts thereof, which comprise a) reacting a compound of the formula (II)

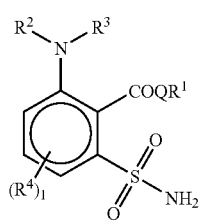

(II)

with a heterocyclic carbamate of the formula (III),

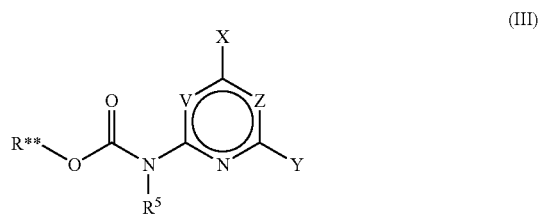

(III)

in which R** is a substituted or unsubstituted $C_1-C_{20}$-hydrocarbon radical, such as aryl or alkyl, preferably unsubstituted or substituted phenyl or unsubstituted or substituted $(C_1-C_4)$alkyl, or b) reacting a sulfonylcarbamate of the formula (IV),

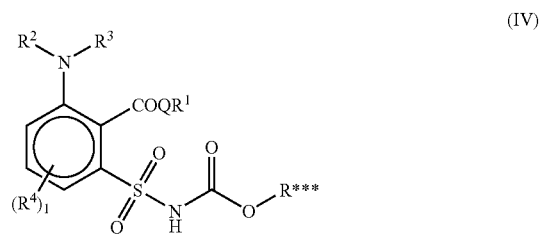

(IV)

in which R*** is a substituted or unsubstituted $C_1-C_{20}$-hydrocarbon radical, such as unsubstituted or substituted phenyl or unsubstituted or substituted $(C_1-C_4)$alkyl, with an amino heterocycle of the formula (V)

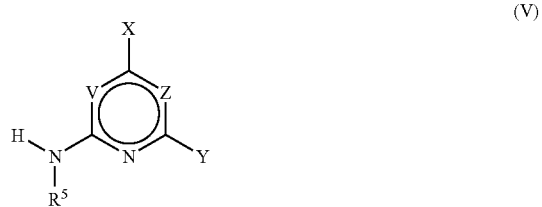

(V)

or c) reacting a sulfonyl isocyanate of the formula (VI)

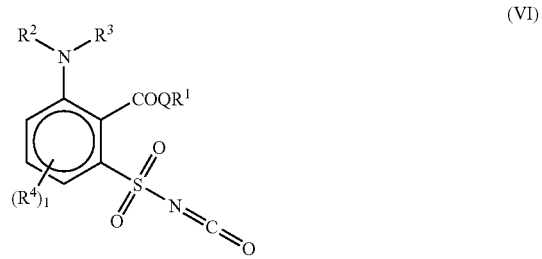

(VI)

with an amino heterocycle of the formula (V) or d) reacting a sulfonamide of the formula (II) with a (thio) isocyanate of the formula (VII)

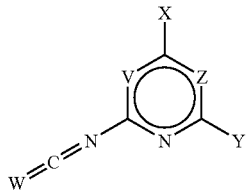
(VII)

in the presence of a base or e) reacting an amino heterocycle of the formula (V) initially under base catalysis with a carbonic ester, for example diphenyl carbonate, and reacting the resulting intermediate in a one-pot reaction with a sulfonamide of the formula (II) (see variant a), or f) reacting a phenylsulfonyl urea of the formula (VIII)

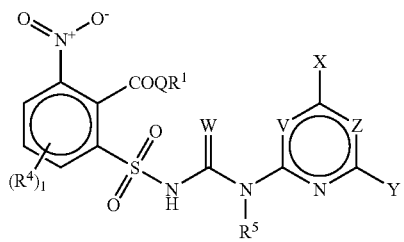
(VIII)

by reduction of the nitro group and, if appropriate, further conversion of the hydroxylamine or amine function that is released to give a sulfonyl urea of the formula (I), where in the formulae (II)-(VIII) the radicals, groups and indices $R^1$-$R^5$, Q, V, W, X, Y, Z and I are as defined in formula (I). Process variants a) to c), e) and f) initially afford compounds of the formula (I) where W=O.

The reaction of the compounds of the formulae (II) and (III) is preferably carried out under base catalysis in an inert organic solvent, such as, for example, dichloromethane, acetonitrile, dioxane or THF, at temperatures between 0° C., preferably 20° C., and the boiling point of the solvent. The base used is, for example, an organic amine base, such as 1,8-diazabicyclo[5.4.0]undec-7-ene (DBU), an alkali metal tert-butoxide, such as, for example, NaO-t-$C_4H_9$, or an alkali metal hydroxide, such as, for example, NAOH, in particular if R=(subst.) phenyl (cf. EP-A-44 807), or trimethylaluminum or triethylaluminum, the latter in particular if R=alkyl (cf. EP-A-166 516). The base in question is employed here, for example, in the range of from 1 to 3 molar equivalents, based on the compound of the formula (II).

The sulfonamides (II) and structurally related compounds of the formulae (IV) and (VI) and the phenylsulfonylureas (VIII) are novel compounds. They, and their preparation, likewise form part of the subject-matter of the present invention.

The compounds of the formula (II) are obtained as shown in Scheme 1, for example starting with compounds of the formula (IX)

Scheme 1

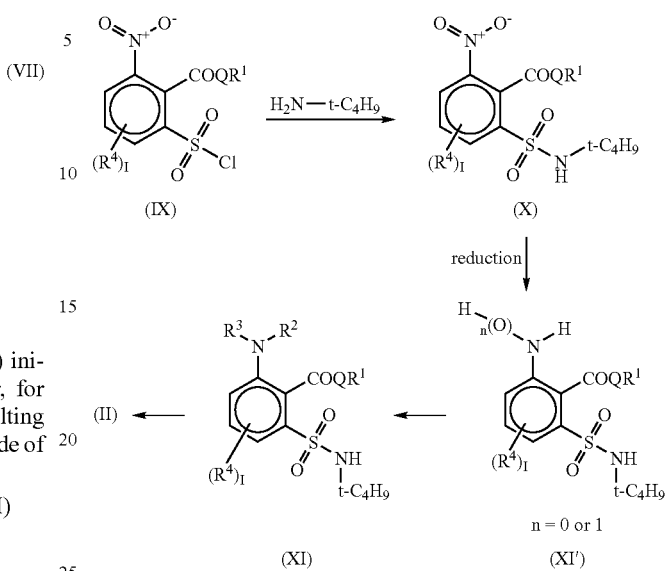

n = 0 or 1

Treatment of sulfonyl chlorides of the formula (IX) with tert-butyl amine gives sulfonamides of the formula (X). By reducing the nitro groups in the compounds of the formula (X), the corresponding hydroxylamines or amines (XI') are obtained, and the functionality that is released can, if appropriate, be derivatized, for example alkylated. The resulting intermediates of the formula (XI) are finally converted into the compounds (II), by treatment with acid. The radicals $R^1$ to $R^4$, Q and I in Scheme 1 are as defined in formula (I).

Sulfonamide formation is carried out, for example, in inert solvents, such as, for example, dichloromethane, tetrahydrofuran (THF), dioxane, toluene or dimethyl-formamide (DMF), at temperatures from −70° C. to the boiling point of the solvent, preferably of up to 25° C. Here, preference is given to using an amount of amine of 1.5-2.5 equivalents, based on the sulfonyl chloride.

The reduction of the nitro function in (X) to amines or hydroxylamines of the formula (XI') is carried out similarly to known methods (cf. Houben-Weyl, "Methoden der Organischen Chemie" [Methods of Organic Chemistry], 4th Ed. Vol. XI/1 pp. 360 ff, Thieme Verlag Stuttgart, 1957 and Vol. X/1 pp. 1138 ff, Thieme Verlag Stuttgart, 1971).

Compounds of the formula (XI') (where n=0), can be subjected to reductive alkylation with carbonyl compounds (cf. Houben-Weyl, "Methoden der Organischen Chemie", 4th Ed. Vol. XI/1 pp. 618-643, Thieme Verlag Stuttgart, 1957; J. Am. Chem. Soc. 96 (1974) 7812-7814; J. Med. Chem. 38 (1995) 3132-3137). By subsequent cleavage of the tert-butyl group, it is possible to prepare, for example, secondary and tertiary anilines of the formula (II).

In the compounds (XI), the tert-butyl protective group is removed by treatment with a strong acid (see WO 89/10921). Suitable strong acids are, for example, mineral acids, such as $H_2SO_4$ or HCl, or strong organic acids, such as trifluoroacetic acid. The reaction is carried out, for example, at temperatures of from −20° C. to the respective reflux temperature of the reaction mixture, preferably at from 0° C. to 40° C. The reaction can be carried out in the absence of a solvent or else in an inert solvent, such as, for example, dichloromethane or trichloromethane.

For I=0, Q=O and R¹=H, Me, Et and allyl, the compounds (IX) are known (see U.S. Pat. No. 4,647,588, U.S. Pat. No. 4,694,020, EP-A-197 386 and U.S. Pat. No. 4,603,133). The novel compounds of the formula (IX) according to the invention can be prepared starting with ring-substituted phthalic acids (for I=0 for example from commercial 3-nitrophthalic acid), similarly to known methods (see J. Heterocyclic Chem. 23 (1986) 1253-1255).

The carbamates of the formula (III) can be prepared by methods as described in the South African Patent Applications 82/5671 and 82/5045, or EP-A-70 804 (U.S. Pat. No. 4,480,101) or RD 275 056.

The reaction of the compounds (IV) with the amino heterocycles (V) is preferably carried out in inert aprotic solvents, such as, for example, dioxane, acetonitrile or tetrahydrofuran, at temperatures between 0° C. and the boiling point of the solvent. The phenylsulfonylcarbamates of the formulae (IV) and (XII) are obtained from compounds of the formulae (II) and (XII), respectively, by the methods of U.S. Pat. No. 4,684,393 or U.S. Pat. No. 4,743,290. The required starting materials (V) are known from the literature or can be prepared by processes known from the literature (see DE-A-38 42 621; Dudley J. R. et al. J. Am. Chem. Soc. 73 (1951) 1968-2990; Braker et al. J. Am. Chem. Soc. 69 (1947) 3072, 3075; Rose et al. J. Chem. Soc. (1946) 81, 84; Huffman, K. R.; Schaefer, F. C. J. Org. Chem. 28 (1963) 1816-1821; Gabriel et al. Chem. Ber. 32 (1899) 2924).

The phenylsulfonyl isocyanates of the formula (VI) can be prepared similarly to U.S. Pat. No. 4,481,029 and reacted with the amino heterocycles (V).

The (thio)isocyanates of the formula (VII) can be obtained by processes known from the literature (EP-A-232 067, EP-A-166 516). The (thio)isocyanates (VII) are reacted with the compounds (II), for example, at from −10° C. to 100° C., preferably at from 20° C. to 100° C., in an inert aprotic solvent, such as, for example, acetone or acetonitrile, in the presence of a suitable base, for example triethylamine or potassium carbonate.

The intermediates of the formula (VIII) can be prepared, for example, by avoiding the isolation of the intermediate sulfonyl isocyanates, directly from the sulfonyl chlorides (IX) and the amino heterocycles (V) in the presence of an alkali metal or ammonium cyanate or thiocyanate and pyridine (cf. U.S. Pat. No. 5,157,119). Alternatively, the compounds (VIII) can also be obtained by reacting a sulfonamide (XII) with carbamates of the formula (III), corresponding to the process described under a). Starting with the sulfonamides (XII), the intermediates of the formula (VIII) can also be prepared by the methods of the processes described under d) and e). Moreover, the intermediates of the formula (VIII) can also be prepared from compounds of the formula (X*) where Z=NHCOOR*, similarly to the process described under b).

The sulfonamides (XII) can be obtained by reacting the compounds (IX) with ammonia (Scheme 2).

Scheme 2

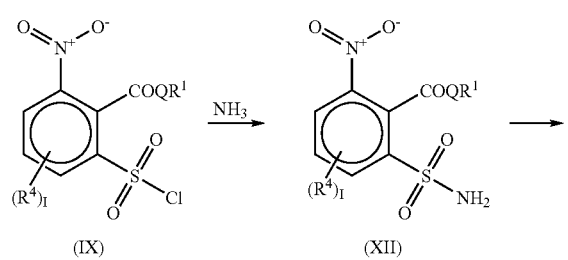

(IX) → (XII)

-continued

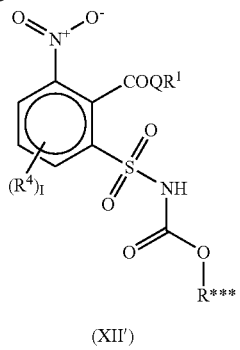

(XII')

The sulfonamide is formed, for example, in aqueous medium or inert solvents, such as, for example ethyl acetate, dichloromethane, tetrahydrofuran (THF), dioxane, toluene or dimethylformamide (DMF), at temperatures from −70° C. to the boiling point of the solvent, preferably up to 25° C. Preference is given, to using an amount of ammonium of 1.5-2.5 equivalents, based on the sulfonyl chloride.

The reaction of an amino heterocycle of the formula (V) with diphenyl carbonate and a sulfonamide of the formula (II) can be, carried out in a one-pot reaction in accordance with EP-A-562 575.

The compounds of the formulae (II), (IV), (VI), (XI) and (XI') mentioned are structurally related novel intermediates of the formula (II*)

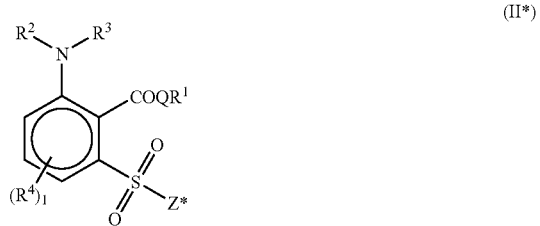

(II*)

in which Z*=NH₂, NHCOOR*, NCO or NH-tert-butyl and R¹-R⁴, I and Q are as defined in formula (I) and R* is as defined in formula (IV).

The abovementioned compounds of the formulae (IX), (X), (XII) and (XII') are structurally related novel intermediates of the formula (X*)

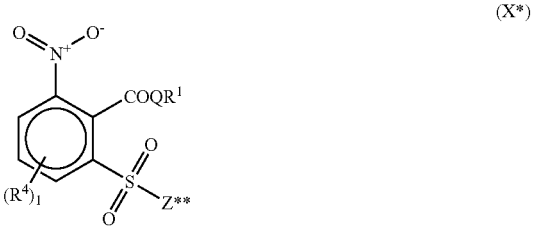

(X*)

in which Z=NH₂, NHCOOR*, NH-tert-butyl or Cl and R¹, R⁴, I and Q are as defined in formula (I) and R* is as defined in formula (IV), except for compounds in which Z=Cl, I=0, Q=O and R¹=H, methyl, ethyl or allyl.

Also novel are the intermediates of the formula (VIII)

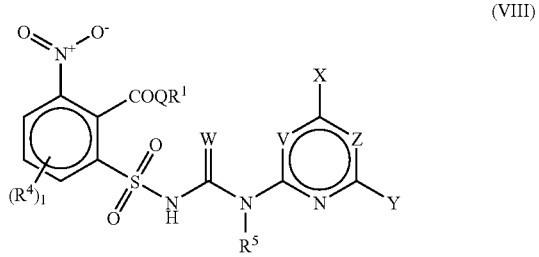

(VIII)

in which $R^1$, $R^4$, $R^5$, Q, V, W, X, Y, Z and I are as defined in formula (I).

The salts of the compounds of the formula (I) are preferably prepared in inert polar solvents, such as, for example, water, methanol or acetone, at temperatures of from 0° C. to 100° C. Suitable bases for preparing the salts according to the invention are, for example, alkali metal carbonates, such as potassium carbonate, alkali metal and alkaline earth metal hydroxides, for example NaOH or KOH, or alkali metal alkoxides, such as sodium methoxide or sodium tert-butoxide, or ammonia or ethanolamine.

The "inert solvents" mentioned in the process variants above are to be understood as meaning in each case solvents which are inert under the reaction conditions in question, but which need not be inert under any reaction conditions.

Collections of compounds of the formula (I) and salts thereof which can be synthesized by the abovementioned scheme may also be prepared in a parallel manner and this may be effected manually or in a semiautomated or fully automated manner. In this case, it is possible, for example, to automate the procedure of the reaction, the work-up or the purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A number of commercially available apparatuses as they are offered by, for example, Stem Corporation, Woodrolfe Road, Tollesbury, Essex, CM9 8SE, England, H+P Labortechnik GmbH, Bruckmannring 28, 85764 Oberschleißheim, Germany or Radleys, Shirehill, Saffron Walden, Essex, CB11 3AZ, England may be used for the parallel procedure of the reaction and work-up. For the parallel purification of compounds of the formula (I) and their salts, or of intermediates obtained during the preparation, use may be made, inter alia, of chromatography apparatuses, for example those from ISCO, Inc., 4700 Superior Street, Lincoln, Nebr. 68504, USA.

The apparatuses mentioned lead to a modular procedure in which the individual process steps are automated, but manual operations have to be performed between the process steps. This can be avoided by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) and salts thereof may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Verlag Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131-5135), in which products from IRORI, 11149 North Torrey Pines Road, La Jola, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSyn Tech GmbH, Wullener Feld 4, 58454 Witten, Germany.

The preparation methods described here give compounds of the formula (I) and their salts in the form of collections of substances known as libraries. The present invention also relates to libraries which contain at least two compounds of the formula (I) and their salts.

The compounds of the formula (I) according to the invention and their salts, hereinbelow together referred to as compounds of the formula (I) (according to the invention), have excellent herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species.

Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Matricaria, Abutilon* and *Sida* from amongst the annuals, and *Convolvulus, Cirsium, Rumex* and *Artemisia* in the case of the perennial weeds.

The active ingredients according to the invention also effect outstanding control of harmful plants which occur under the specific conditions of rice growing such as, for example, *Echinochloa, Sagittaria, Alisma, Eleocharis, Scirpus* and *Cyperus*.

If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledonous weeds, crop plants of economically important crops, for example, dicotyledonous crops such as soya, cotton, oilseed rape, or sugar beet, or gramineous crops such as wheat, barley, rye, rice or corn, in particular soya, are not damaged at all, or only to a negligible extent. For these reasons, the present compounds are highly suitable for selectively controlling undesired plant growth in plantings for agricultural use or in plantings of ornamentals.

In addition, the substances according to the invention have outstanding growth-regulating properties in crop plants. They engage in the plant metabolism in a regulating manner and can thus be employed for the targeted control of plant constituents and for facilitating harvesting, for example, by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced here by, or prevented completely.

Owing to their herbicidal and plant growth-regulatory properties, the active compounds can also be employed for controlling harmful plants in crops of known or still to be developed genetically engineered, plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested product are known.

The use of the compounds of the formula (I) according to the invention or their salts in economically important transgenic crops of useful and ornamental plants, for example of cereal, such as wheat, barley, rye, oats, millet, rice, maniok and corn, or else in crops of sugar beet, cotton, soya, oilseed rape, potato, tomato, pea and other vegetable species is preferred.

The compounds of the formula (I) can preferably be used as herbicides in crops of useful plants which are resistant or which have been made resistant by genetic engineering toward the phytotoxic effects of the herbicides.

Conventional, ways of preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827 and WO. 91/19806), transgenic crop plants which are resistant to certain herbicides of the glufosinate- (cf., for example, EP-A 0 242 236, EP-A 0 242 246) or glyphosate-type (WO 92/00377), or of the sulfonylurea-type (EP-A 0 257 993, U.S. Pat. No. 5,013,659), transgenic crop plants, for example cotton, having, the ability to produce Bacillus thuringiensis toxins (Bt toxins) which impart resistance to certain pests to the plants (EP-A 0 142 924, EP-A 0 193 259), transgenic crop plants, having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold. Spring. Harbor, N.Y.; or Winnacker "Gene und Klone" [Genes and Clones], VCH Weinheim, 2nd edition 1996, or Christou, "Trends in Plant Science" 1 (1996) 423-431).

In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end, it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (19902), 32193227; Wolter et al., Proc. Natl. Acad. Sci. USA 85 (1988), 846-850; Sonnewald et al., Plant j. 1 (1991), 95-106).

The transgenic plant cells can be regenerated to whole plants using known techniques. The transgenic plants can in principle be plants of any desired plant species, i.e. both monocotyledonous and dicotyledonous plants.

In this manner, it is possible to obtain transgenic plants which have modified properties by overexpression, suppression or inhibition of homologous (=natural) genes or gene sequences or by expression of heterologous (=foreign) genes or gene sequences.

The compounds according to the invention can preferably be used in transgenic crops which are resistant to herbicides selected from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants.

The invention therefore also provides for the use of the compounds (I) according to the invention as herbicides for controlling harmful plants in transgenic crop plants.

The compounds according to the invention can be applied in the customary formulations in the form of wettable powders, emulsifiable concentrates, sprayable solutions, dusts or granules. The invention therefore also provides herbicidal and plant growth-regulating compositions comprising compounds of the formula (I).

The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes.

These individual formulation types are known in principle and are described, for example, in Winnacker-Küchler, "Chemische Technologie" [Chemical Technology], Volume 7, C. Hauser Verlag Munich, 4th edition 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation auxiliaries, such as inert materials, surfactants, solvents and other additives, are likewise known and are described, for example, in: Watkins, "Handbook of Insecticide Dust Diluents and Carriers", 2nd ed., Darland Books, Caldwell. N.J., H.v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Greenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th edition 1986.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines; fatty alcohol polyglycol ethersulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills-and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th ed., McGraw-Hill, New York 1973, pp. 8-57.

For further details on the formulation of crop protection products, see for example G. C. Klingman, 'Weed Control as a Science', John Wiley and Sons., Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations generally contain from 0.1 to 0.99% by weight, in particular from 0.1 to 95% by weight, of active compound of the formula (I).

In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules, the content of active compound depends partly on whether the active compound, is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Suitable active compounds which can be combined with the active compounds according to the invention in mixed formulations or in a tank mix are, for example, known active compounds, whose effect is based on an inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26, 441-445 (1986), or "The Pesticide Manual", 11th edition, The British Crop Protection Council and the Royal Soc. of Chemistry, 1997 and in the literature cited therein. For example, the following active compounds may be mentioned as herbicides which are known and which can be combined with the compounds of the formula (I) (note: the compounds are either referred to by the "common name" in accordance with the International Organization for Standardization (ISO) or by the chemical names, if appropriate together with a customary code number):

acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone; amidosulfuron; amitrol; AMS, i.e. ammonium sulfamate; anilofos; asulam; atrazine; azafenidin; azimsulfuron; aziprotryn; barban; BAS 516H, i.e. 5-fluoro-2-phenyl-4H-3,1-benzoxazin-4-one; beflubutamide; benazolin(-ethyl); benfluralin; benfuresate; bensulfuron(-methyl); bensulide; bentazone; benzobicyclone; benzofenap; benzofluor; benzoylprop(-ethyl); benzthiazuron; bialaphos; bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole; caloxydim; carbetamide; cafentrazone(-ethyl); CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurecol-methyl; chloridazon; chlorimuron(-ethyl); chlormesulan (ICI-A0051); chlornitrofen; chlorotoluron; chloroxuron; chlorpropham; chlorsulfuron; chlorthal(-dimethyl); chlorthiamid; cinidon (-ethyl and -methyl); cinmethylin; cinosulfuron; clefoxydim, clethodim; clodinafop and its ester derivatives (for example clodinafop-propargyl); clomazone; clomeprop; cloproxydim; clopyralid; clopyrasulfuron(-methyl); cloransulam(-methyl); cumyluron; cyanazine; cycloate; cyclosulfamuron; cycloxydim; cycluron; cyhalofop and its ester derivatives (for example cyhalofop-butyl); cyperquat; cyprazine; cyprazole; daimuron; 2,4-D; 2,4-DB; dalapon; desmedipham; desmetryn; di-allate; dicamba; dichlobenil; dichlorprop; diclofop and its esters such as diclofop-methyl; didosulam, i.e. N-(2,6-dichlorophenyl)-5-ethoxy-7-fluoro-[1,2,4]triazolo[1,5-c]pyrimidine-2-sulfonamide; diethatyl(-ethyl); difenoxuron; difenzoquat; diflufenican; diflufenzopyr(-sodium); dimefuron; dimepiperate; dimethachlor; dimethametryn; dimethenamid; dimidazon; dimethipin; dinitramine; dinoseb; dinoterb; diphenamid; dipropetryn; diquat; dithiopyr; diuron; DNOC; eglinazineethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron(-methyl); ethidimuron; ethiozin; ethofumesate; ethoxyfen and its esters (for example ethyl acetate, HN-252); ethoxysulfuron; etobenzamid; F5231, i.e. N-[2-chloro-4-fluoro-5-[4-(3-fluoropropyl)-4,5-dihydro-5-oxo-1H-tetrazol-1-yl]-phenyl]ethanesulfonamide; fenoprop; fenoxan, fenoxaprop and fenoxaprop-P and their esters, for example fenoxaprop-P-ethyl and fenoxaprop-ethyl, fenoxydim; fentrazamide; fenuron; flamprop(-methyl or -isopropyl or -isopropyl-L); flazasulfuron; florasulam; fluazifop and fluazifop-P and their esters (for example fluazifop-butyl and fluazifop-P-butyl); fluazolate(-isopropazol); flucarbazone (-sodium); fluchloralin; flufenacet; flumetsulam; flumeturon; flumiclorac and its esters (for example flumicloracpentyl); flumioxazin; flurmipropyn; fluometuron; flupoxam (KNW-739); fluorodifen; fluoroglycofen(-ethyl); flupropacil flupyrsulfuron(-methyl, -sodium); flurenol (-butyl); fluridone; flurochloridone; fluroxypyr(-meptyl); flurtamone; fluthiacet(-methyl); fluthiamide; fomesafen; foramsulfuron; fosamine; furyloxyfen; glufosinate(-ammonium); glyphosate(-isopropylammonium); halosafen; halosulfuron(-methyl); haloxyfop and its esters; haloxyfop-P (=R-haloxyfop) and its esters; hexazinone; imazamethabenz; imazamox; imazapic; imazapyr; imazaquin(-ammonium); imazethamethapyr; imazethapyr; imazosulfuron; iridanofan; iodosulfuron; ioxynil; isocarbamid; isopropalin; isoproturon; isouron; isoxaben; isoxachlortole; isoxaflutole; isoxapyrifop; karbutilate; lactofen; lenacil; linuron; MCPA; MCPB; mecoprop; mefenacet; mefluidid; mesotrione; metarmitron; metazachlor; methabenzthiazuron; metham; methazole; methoxyphenone; methyldymron; metobenzuron; metobromuron; (alpha-)metolachlor; metosulam; metoxuron; metribuzin; metsulfuron(-methyl); MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyly)-1-methyl-5-benzyloxypyrazole;

neburon; nicosulfuron; nipyraclophen; nitralin; nitrofen; nitrofluorfen; norflurazon; orbencarb; oryzalin; oxaciclomefone; oxadiargyl; oxadiazone; oxasulfuron; oxyfluorfen; paraquat; pebulate; pelargonic acid; pendimethalin; pentoxazone; perfluidone; phenisopham; phenmedipham; picloram; picolinafen; piperophos; piributicarb; pirifenop (-butyl); pretilachlor; primisulfuron(-methyl); procarbazone(-sodium); procyazine; prodiamine; profluralin; proglinazine(-ethyl); prometon; prometryn; propachlor; propanil; propaquizafop and its esters; propazine; propham; propisochlor; propyzamide; prosulfalin; prosulfocarb; prosulfuron; prynachlor; pyroflufen (-ethyl); pyrazolinate; pyrazon; pyrazosulfuron(-ethyl); pyrazoxyfen; pyribenzoxim; pyributicarb; pyridafol; pyridate; pyriminobac(-methyl); pyrithiobac(-sodium); pyroxofop and its esters (for example pyroxofop-propargyl); quinclorac, quinmerac; quinofop and its ester derivatives, quinodamine; quizalofop and quizalofop-P and their ester derivatives, (for example quizalofop-ethyl; quizalofop-P-tefuryl and ethyl); renriduron; rimsulfuron; S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[-[2-chloro-4-(trifluoromethyl)phenoxy]2-naphthalenyl]-oxy]propanoic acid and its methyl ester; sulcotrione; sulfentrazone; sulfazurone; sulfometuron(-methyl); sulfosate (ICI-A0224); sulfosulfuron; TCA(-sodium); tebutam; tebuthiuron; tepraloxydim; terbacil; terbucarb; terbuchlor; terbumeton; terbuthylazine, terbutryn, TFH 450, i.e. N,N-diethyl-3[(2-ethyl-6-methylphenyl)sulfonyl]1H-1,2,4-triazole-1-carboxamide; thenylchlor; thiafluamide; thiazafluron; thiazopyr; thidiazimin (SN-24085); thifensulfuron(-methyl); thiobencarb; tiocarbazil; tralkoxydim; tri-allate; triasulfuron; triaziflam; triazofenamide; tribenuron(-methyl); tridopyr; tridiphane; trietazine; trifluralin; triflusulfuron(-methyl); tritosulfuron; trimeturon; tsitodef; vernolate; WL 110547, i.e. 5-phenoxy-1-[3-(trifluoromethyl)phenyl]-1H-tetrazole; AMS-13668; D489; BH-60229; BH-71712, DK-8910; DOWCO-535; DPX-N8189; JTC-101; KH-218; KPP-300; KPP-421; LS 82-556; MBH-001; MT-146; MT;-147; NC-324; NC-330; OK-9403; OK-9604; OK-9701; PP-600; SC-0774 and UBH-509.

The active compounds according to the invention can also be used in combination with one or more compounds which act as safeners. Examples of safeners are:

a) Compounds of the formulae (XIII) to (XV),

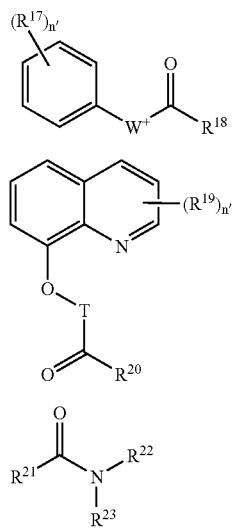

where the symbols and indices are as defined below:

n' is a natural number from 0 to 5, preferably from 0 to 3;

T is a ($C_1$ or $C_2$)alkanediyl chain which is unsubstituted or substituted by one or two ($C_1$-$C_4$)alkyl radicals or by [($C_1$-$C_3$)alkoxy]carbonyl;

$W^+$ is an unsubstituted or substituted divalent heterocyclic radical selected from the group consisting of the partially unsaturated or aromatic five-membered heterocycles having 1 to 3 hetero ring atoms of the type N or O, where at least one nitrogen atom and at most one oxygen atom is contained in the ring, preferably a radical from the group ($W^+1$) to ($W^+4$);

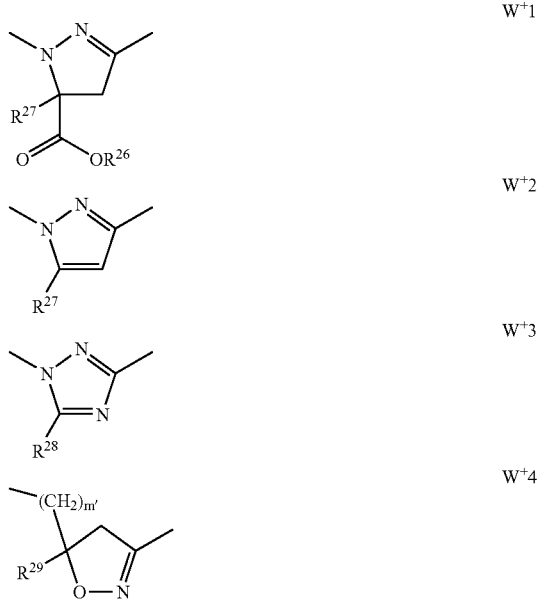

m' is 0 or 1;

$R^{17}$, $R^{19}$ are identical or different and are hydrogen, halogen, ($C_1$-$C_4$)alkyl, ($C_1$-$C_4$)alkoxy, nitro or ($C_1$-$C_4$)haloalkyl;

$R^{18}$, $R^{20}$ are identical or different and are $OR^{24}$, $SR^{24}$ or $NR^{24}R^{25}$ or a saturated or unsaturated 3- to 7-membered heterocycle having at least one nitrogen atom and up to 3 heteroatoms, preferably selected from the group consisting of O and S, which is attached via the nitrogen atom with the carbonyl group in (XIII) or (XIV) and which is unsubstituted or substituted by radicals selected from the group consisting of ($C_1$-$C_4$)alkyl, ($C_1$-$C_4$)alkoxy or unsubstituted or substituted phenyl, preferably a radical of the formula $OR^{24}$, $NHR^{25}$ or $N(CH_3)_2$, in particular of the formula $OR^{24}$;

$R^{24}$ is hydrogen or an unsubstituted or substituted aliphatic hydrocarbon radical, preferably having a total of from 1 to 18 carbon atoms;

$R^{25}$ is hydrogen, ($C_1$-$C_6$)alkyl, ($C_1$-$C_6$)alkoxy or substituted or unsubstituted phenyl;

$R^{26}$ is hydrogen, ($C_1$-$C_8$)alkyl, ($C_1$-$C_8$)haloalkyl, ($C_1$-$C_4$)alkoxy-($C_1$-$C_4$)alkyl, ($C_1$-$C_6$)hydroxyalkyl, ($C_3$-$C_{12}$)cycloalkyl or tri-($C_1$-$C_4$)alkylsilyl;

$R^{27}$, $R^{28}$, $R^{29}$ are identical or different and are hydrogen, ($C_1$-$C_8$)alkyl, ($C_1$-$C_8$)haloalkyl, ($C_3$-$C_{12}$)cycloalkyl or substituted or unsubstituted phenyl;

$R^{21}$ is ($C_1$-$C_4$)alkyl, ($C_1$-$C_4$)haloalkyl, ($C_2$-$C_4$)alkenyl, ($C_2$-$C_4$)haloalkenyl, ($C_3$-$C_7$)cycloalkyl, preferably dichloromethyl:

$R^{22}$, $R^{23}$ are identical or different and are hydrogen, ($C_1$-$C_4$)alkyl, ($C_2$-$C_4$)alkenyl, ($C_2$-$C_4$)alkynyl, ($C_1$-$C_4$)haloalkyl, ($C_2$-$C_4$)haloalkenyl, ($C_1$-$C_4$)alkylcarbamoyl($C_1$-$C_4$)alkyl, ($C_2$-$C_4$)alkenylcarbamoyl($C_1$-$C_4$)alkyl, ($C_1$-$C_4$)alkoxy ($C_1$-$C_4$)alkyl, dioxolanyl-($C_1$-$C_4$)alkyl, thiazolyl, furyl, furylalkyl, thienyl, piperidyl, substituted or unsubstituted phenyl, or $R^{22}$ and $R^{23}$ together form a substituted or unsubstituted heterocyclic ring, preferably an oxazolidine, thiazolidine, piperidine, morpholine, dihydropyrimidine or benzoxazine ring; or b) one or more compounds selected from the group consisting of:

1,8-naphthalic anhydride,
methyl diphenylmethoxyacetate,
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone 0-1,3-dioxolan-2-ylmethyloxime (fluxofeninm),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolane (MG-191),
N-(4-methylphenyl)-N'-(1-methyl-1-phenylethyl)urea (dymron),
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MGPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor)
and their salts and esters, preferably ($C_1$-$C_8$) esters;
c) N-acylsulfonamides of the formula (XVI) and their salts

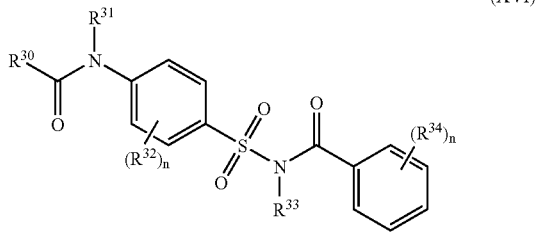

(XVI)

in which
$R^{30}$ is hydrogen, a hydrocarbon radical, a hydrocarbon-oxy radical, a hydrocarbon-thio radical or a heterocyclyl radical, each of the 4 last-mentioned radicals being unsubstituted or being substituted by one or more identical or different radicals selected from the group consisting of halogen, cyano, nitro, amino, hydroxyl, carboxyl, formyl, carboxamide, sulfonamide and radicals of the formula $Z^a$-$R^a$,
each hydrocarbon moiety Preferably having 1 to 20 carbon atoms and a carbon-containing radical $R^{30}$ inclusive of substituents preferably having 1 to 30 carbon atoms;
$R^{31}$ is hydrogen or ($C_1$-$C_4$)alkyl, preferably hydrogen, or
$R^{30}$ and $R^{31}$ together with the group of the formula —CO—N— are the radical of a 3- to 8-membered saturated or unsaturated ring;
$R^{32}$ is identical or different halogen, cyano, nitro, amino, hydroxyl, carboxyl, formyl, $CONH_2$, $SO_2NH_2$ or a radical of the formula $Z^b$-$R^b$;
$R^{33}$ is hydrogen or ($C_1$-$C_4$)alkyl, preferably H;

$R^{34}$ is identical or different to halogen, cyano, nitro, amino, hydroxyl, carboxyl, CHO, $CONH_2$, $SO_2NH_2$ or a radical of the formula. $Z^c$-$R^c$;
$R^a$ is a hydrocarbon radical or a heterocyclyl radical, each of the two last-mentioned radicals being unsubstituted or substituted by one or more identical or different radicals selected from the group consisting of halogen, cyano, nitro, amino, hydroxyl, mono- and di-[($C_1$-$C_4$)alkyl]amino, or an alkyl radical in which a plurality, preferably 2 or 3, non-adjacent $CH_2$ groups are in each case replaced by one oxygen atom;
$R^b$,$R^c$ are identical or different and are a hydrocarbon radical or a heterocyclyl radical, each of the two last-mentioned radicals being unsubstituted or substituted by one or more identical or different radicals selected from the group consisting of halogen, cyano, nitro, amino, hydroxyl, phosphoryl, halo($C_1$-$C_4$)alkoxy, mono- and di-[($C_1$-$C_4$)alkyl]amino, or an alkyl radical in which a plurality, preferably 2 or 3, non-adjacent $CH_2$ groups are replaced in each case by one oxygen atom;
$Z^a$ is a divalent group of the formula —O—, —S—, —CO—, —CS—, —CO—O—, —CO—S—, —O—CO—, —S—CO—, —SO—, —$SO_2$—, —$NR^+$—, —CO—$NR^+$—, —$NR^+$—CO—, —$SO_2$—$NR^+$— or —$NR^+$—$SO_2$—, the bond given on the right-hand side of each of the divalent groups being the bond to the radical $R^a$, and the radicals $R^+$ in the 5 last-mentioned radicals independently of each other being in each case H, ($C_1$-$C_4$)alkyl or halo ($C_1$-$C_4$)alkyl;
$Z^b$,$Z^c$ independently of one another are a direct bond or a divalent group of the formula —O—, —S—, —CO—, —CS—, —CO—O—, —CO—S—, —O—CO—, —S—CO—, —SO—, —$S_2$—, —$NR^+$—, —$SO_2$—$NR^+$—, —$NR^+$—$SO_2$—, —CO—$NR^+$— or —$NR^+$—CO—, the bond given on the right-hand side of each of the divalent groups being the bond to the radical $R^b$ or $R^c$ and where the radicals $R^+$ in the 5 last-mentioned radicals independently of one another are in each case. H, ($C_1$-$C_4$) alkyl or halo($C_1$-$C_4$)alkyl;
n is an integer from 0 to 4, preferably 0, 1 or 2, in particular 0 or 1, and
m is an integer from 0 to 5, preferably 0, 1, 2 or 3, in particular 0, 1 or 2;
d) acylsulfamoylbenzamides of the formula (XVII), optionally also in salt form,

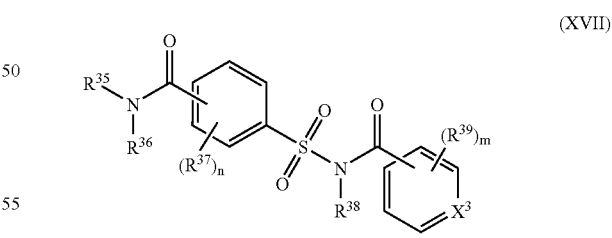

(XVII)

in which
$X^3$ is CH or N;
$R^{35}$ is hydrogen, heterocyclyl or a hydrocarbon radical, the two last-mentioned radicals optionally being substituted by one or more identical or different radicals selected from the group consisting of halogen, cyano, nitro, amino, hydroxyl, carboxyl, CHO, $CONH_2$, $SO_2NH_2$ and $Z^a$-$R^a$;
$R^{36}$ is hydrogen, hydroxyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, the five last-mentioned radicals optionally being substituted by one or more identical or different radicals selected from the group consisting of halogen, hydroxyl, $(C_1-C_4)$alkyl, $(C_1-C_4)$alkoxy and $(C_1-C_4)$alkylthio, or $R^{35}$ and $R^{36}$ together with the nitrogen atom to which they are attached are a 3- to 8-membered saturated or unsaturated ring;

$R^{37}$ is halogen, cyano, nitro, amino, hydroxyl, carboxyl, CHO, $CONH_2$, $SO_2NH_2$ or $Z^b-R^b$;

$R^{38}$ is hydrogen, $(C_1-C_4)$alkyl, $(C_2-C_4)$alkenyl or $(C_2-C_4)$alkynyl;

$R^{39}$ is halogen, cyano, nitro, amino, hydroxyl, carboxyl, phosphoryl, CHO, $CONH_2$, $SO_2NH_2$ or $Z^c-R^c$;

$R^d$ is a $(C_2-C_{20})$alkyl radical whose carbon chain is interrupted once or more than once by oxygen atoms, or is heterocyclyl or a hydrocarbon radical, the two last-mentioned radicals optionally being substituted by one or more identical or different radicals selected from the group consisting of halogen, cyano, nitro, amino, hydroxyl, mono- and di-[$(C_1-C_4)$alkyl]amino;

$R^b$, $R^c$ are identical or different and are a $(C_2-C_{20})$alkyl radical whose carbon chain is interrupted once or more than once by oxygen atoms, or a heterocyclyl or a hydrocarbon radical, the two last-mentioned radicals optionally being substituted by one or more identical or different radicals selected from the group consisting of halogen, cyano, nitro, amino, hydroxyl, phosphoryl, $(C_1-C_4)$-haloalkoxy, mono- and di-[$(C_1-C_4)$alkyl]amino;

$Z^a$ is a divalent unit selected from the group consisting of O, S, CO, CS, C(O)O, C(O)S, SO, $SO_2$, $NR^d$, $C(O)NR^d$ or $SO_2NR^d$;

$Z^b$, $Z^c$ are identical or different and are a direct bond or a divalent unit selected from the group consisting of O, S, CO, CS, C(O)O, C(O)S, SO, $SO_2$, $NR^d$, $SO_2NR^d$ or $C(O)NR^d$;

$R^d$ is hydrogen, $(C_1-C_4)$alkyl or $(C_1-C_4)$haloalkyl;

n is an integer from 0 to 4, and m in the event that X is CH, is an integer from 0 to 5 and, in the event that X is N, is an integer from 0 to 4;

e) compounds of the formula (XVIII),

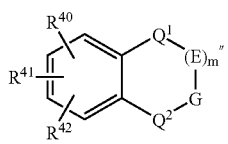

(XVIII)

in which the symbols and indices have the following meanings:

$R^{40}$ is H, $(C_1-C_4)$alkyl, $(C_1-C_4)$alkyl substituted by $(C^1-C_4)$alkyl-$X^4$ or $(C_1-C_4)$haloalkyl-$X^4$, $(C_1-C_4)$haloalkyl, $NO_2$, CN, —COO—$R^{43}$, $NR_2^{44}$, $SO_2NR_2^{45}$ or $CONR_2^{46}$;

$R^{41}$ is H, halogen, $(C_1-C_4)$alkyl, $CF_3$, $(C_1-C_4)$alkoxy or $(C_1-C_4)$-haloalkoxy;

$R^{42}$ is H, halogen or $(C_1-C_4)$alkyl;

$Q^1$, $Q^2$, E, G are identical or different, —O—, —S—, —$CR_2^{47}$—, —CO—, —$NR^{48}$— or a group of the formula (XIX),

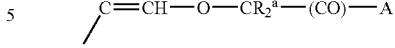

(XIX)

with the proviso that a) at least one of the groups $Q^1$, $Q^2$, E, G is a carbonyl group, that exactly one of these groups is a radical of the formula (XIX) and that the group of the formula (XIX) is adjacent to a carbonyl group, and b) two adjacent groups $Q^1$, $Q^2$, E and G cannot simultaneously be oxygen;

$R^a$ is identical or different H or $(C_1-C_8)$alkyl or the two radicals $R^9$ together are $(C_2-C_6)$alkylene;

A is $R^b-Y^3$— or —$NR_2^{49}$;

$X^4$ is —O— or —$S(O)_p$—;

$Y^3$ is —O— or —S—;

$R^b$ is H, $(C_1-C_8)$alkyl, $(C_1-C_8)$haloalkyl, $(C_1-C_4)$alkoxy($C_1-C_8$)alkyl, $(C_3-C_6)$alkenyloxy($C_1-C_8$)alkyl, or phenyl($C_1-C_8$)alkyl, where the phenyl ring is optionally substituted by halogen, $(C_1-C_4)$alkyl, $CF_3$, methoxy or methyl-$S(O)_p$; $(C_3-C_6)$alkenyl, $(C_3-C_6)$haloalkenyl, phenyl($C_3-C_6$)alkenyl, $(C_3-C_6)$alkynyl, phenyl($C_3-C_6$)alkynyl, oxetanyl, furfuryl, tetrahydrofuryl;

$R^{43}$ is H or $(C_1-C_4)$alkyl;

$R^{44}$ is identical or different H, $(C_1-C_4)$alkyl, $(C_1-C_4)$alkylcarbonyl or the two radicals $R^{44}$ together are $(C_4-C_5)$alkylene;

$R^{45}$, $R^{46}$ independently of one another are in each case identical or different H, $(C_1-C_4)$alkyl, or the two radicals $R^{45}$ and/or $R^{46}$ together are $(C_4-C_5)$alkylene, where one $CH_2$ group can be replaced by O or S or one or two $CH_2$ groups can be replaced by —$NR^c$—;

$R^c$ is H or $(C_1-C_8)$alkyl;

$R^{47}$ is identical or different H, $(C_1-C_8)$alkyl or the two radicals $R^{47}$ together are $(C_2-C_6)$alkylene;

$R^{48}$ is —H, $(C_1-C_8)$alkyl, substituted or unsubstituted phenyl, or benzyl which is unsubstituted or substituted on the phenyl ring;

$R^{49}$ is identical or different H, $(C_1-C_8)$alkyl, phenyl, phenyl $(C_1-C_8)$alkyl, where a phenyl ring can be substituted by F, Cl, Br, $NO_2$, CN, $OCH_3$, $(C_1-C_4)$alkyl or $CH_3SO_2$—; $(C_1-C_4)$alkoxy($C_1-C_8$)alkyl, $(C_3-C_6)$alkenyl, $(C_3-C_6)$alkynyl, $(C_3-C_6)$cycloalkyl or two radicals $R^{49}$ together are $(C_4-C_5)$ alkylene, where one $CH_2$ group can be replaced: by O or S or one or two $CH_2$ groups can be replaced by —$NR^d$—;

$R^d$ is H or $(C_1-C_4)$alkyl;

m" is 0 or 1 and p is 0, 1 or 2;

inclusive of the stereoisomers and the agriculturally customary salts.

For use, the formulations which are present in commercially available form are, if appropriate, diluted in the customary manner, for example using water in the case of wettable powders, emulsifiable concentrates, dispersions and water-dispersible granules. Preparations in the form of dusts, granules for soil application or broadcasting and sprayable solutions are usually not further diluted with other inert substances prior to use.

The application rate of the compounds of the formula (I) required varies with the external conditions, such as temperature, humidity, the nature of the herbicide used and the like. It can vary within wide limits, for example between 0.001 and 10.0 kg/ha or more of active substance, but it is preferably between 0.005 and 5 kg/ha.

EXAMPLES

A. Chemical Examples

Example A1

Methyl 2-[(tert-butylamino)sulfonyl]-6-nitrobenzoate

At 0° C., 1.4 ml (13.3 mmol) of tert-butylamine are added dropwise to a solution of 1.00 g (3.58 mmol) of methyl-2-(chlorosulfonyl)-6-nitrobenzoate in 8 ml of dichloromethane, and the reaction mixture is then allowed to warm to room temperature. After 2 h, the reaction mixture is poured into ice-water, adjusted to pH 3 using 2 N aqueous hydrochloric acid and extracted with dichloromethane. The organic phase is then dried over sodium sulfate, filtered off and concentrated to dryness under reduced pressure. The residue that remains is digested with diethyl ether and filtered off with suction. This gives 1.06 g (91% of theory) of methyl 2-[(tert-butylamino)sulfonyl]-6-nitrobenzoate of m.p. 89-91° C.

Example A2

Methyl 2-(aminosulfonyl)-6-nitrobenzoate 300 mg (0.948 mmol) of methyl 2-[(tert-butylamino)sulfonyl]-6-nitrobenzoate in 8 ml of trifluoroacetic acid are stirred at room temperature for 4 h. The mixture is subsequently concentrated to dryness under reduced pressure and the residue is digested with diethyl ether. After filtration with suction and drying, 230 mg (93% of theory) of methyl 2-(aminosulfonyl)-6-nitrobenzoate of m.p. 227-229° C. remain.

Example A3

Methyl 2-[(tert-butylamino)sulfonyl]-6-(isopropylamino)benzoate

At a temperature of 5-10° C., 925 mg (24.4 mmol) of sodium borohydride are stirred into 14 ml of acetic acid. After 1 h, this mixture is admixed first with 1.42 g (24.4 mmol) of acetone and then with 700 mg (2.44 mmol) of methyl 2-amino-6-[(tert-butylamino)sulfonyl]benzoate and stirred at 5-10° C. for 2.5 h. For work-up, the reaction mixture is poured into ice-water, neutralized with aqueous ammonia solution and extracted with dichloromethane. The organic phase is concentrated and the residue that remains is triturated with diisopropyl ether. After filtration with suction and drying, 700 mg (89% of theory) of methyl 2-[(tert-butylamino)sulfonyl]-6-(isopropylamino)benzoate remain as a white solid of m.p. 110-112° C.

Example A4

Methyl 2-amino-6-[(tert-butylamino)sulfonyl]benzoate

A solution of 8.00 g (25.3 mmol) of methyl 2-[(tert-butylaminoysulfonyl]-6-nitrobenzoate is admixed with 3.2 g of palladium on activated carbon (5%) and hydrogenated at room temperature and under atmospheric pressure for 6 h. The reaction mixture is then filtered, the filtrate is concentrated to dryness and the residue is purified by silica gel chromatography [TLC (SiO$_2$) ethyl acetate/n-heptane 1:1; R$_f$=0.38] using ethyl acetate/n-heptane (1:1). Evaporation gives 6.23 g (86% of theory) of methyl 2-amino-6-[(tert-butylamino)sulfonyl]benzoate as a beige solid of melting point 132-133° C.

Example A5

Methyl 2-(diisobutylamino)-6-[([(4,6-dimethoxy-2-pyrimidinyl)amino]carbonyl-amino)sulfonyl]benzoate 700 mg (2.04 mmol) of methyl 2-(diisobutylamino)-6-(sulfonylamino)benzoate and 619 mg (2.25 mmol) of phenyl N-(4,6-dimethoxypyrimidin-2-yl)carbamate are initially charged in 10 ml of acetonitrile. At room temperature, '375 mg (2.51 mmol) of 1,8-diazabicyclo[5.4.0]undec-7-ene (1,5-5) (DBU) are then added dropwise, and the reaction mixture is stirred at this temperature for 3 h. The mixture is then poured into ice-water and the solution is slowly adjusted to pH 1 using 2. N hydrochloric acid. The precipitated solid is filtered off with suction, washed with water and dried. This gives 910 mg (91% of theory) of methyl 2-(diisobutylamino)-6-[([(4,6-dimethoxy-2-pyrimidinyl)amino]carbonylamino)sulfonyl]benzoate of m.p. 166-167° C.

Example A6

Methyl 2-[([(4,6-dimethoxy-1,3,5-triazin-2-yl)amino]carbonylamino)sulfonyl]-6-nitrobenzoate At 55-60° C. and under argon, a solution of 5.0 g (17.9 mmol) of methyl 2-chlorosulfonyl-6-nitrobenzobate in 55 ml of dry dichloromethane is added dropwise over 2 h to a suspension of 2.79 g (17.9 mmol) of 2-amino-4,6-dimethoxy-1,3,5-triazine, 1.28 g (19.7 mmol) of sodium cyanate, 1.45 ml (17.9 mmol) of pyridine and 500 mg of freshly activated molecular sieve (pore size 3 Å) in 85 ml of dry acetonitrile. After 7 h of stirring at this temperature, the mixture is allowed to warm to room temperature. After a further 12 h, the reaction mixture is, concentrated and the residue is suspended in 200 ml of water and adjusted to pH 10 using 2 N aqueous sodium hydroxide solution. The precipitated solid is filtered off with suction and the filtrate is extracted with ethyl acetate. The organic phase is separated off and the aqueous phase is adjusted to pH 1.5 using 3 N aqueous hydrochloric acid solution and stirred in an ice bath for 15 min. The precipitated solid is then filtered off with suction, washed first with water and then with methanol and dried under reduced pressure. This gives 2.88 g (36% of theory) of methyl 2-[([(4,6-dimethoxy-1,3,5-triazin-2-yl)amino]carbonylamino)sulfonyl]-6-nitrobenzoate of m.p. 185-195° C. (decomp.).

Example A7

Methyl 2-amino-6-[([(4,6-dimethoxy-1,3,5-triazin-2-yl)amino]carbonylamino)-sulfonyl]benzoate 50 mg (113 µmol) of methyl 2-[([(4,6-dimethoxy-1,3,5-triazin-2-yl)amino]-carbonylamino)sulfonyl]-6-nitrobenzoate are suspended in a mixture of 3 ml of methanol/dimethylformamide (5:1), admixed with 10 mg. of palladium on activated carbon (5%) and 1 mg (8.20 µmol) of sodium (meta) vanadate and, hydrogenated under atmospheric pressure and at room temperature for 3 h. The mixture is then filtered off, the filtrate is concentrated and the residue is taken up in water and adjusted to pH 1.5 using 3 N aqueous hydrochloric acid solution. The precipitate is stirred in an ice-bath for 10 min and then filtered off with suction and dried under reduced pressure. This gives 41 mg (87% of theory) of methyl 2-amino-6-[([(4,6-dimethoxy-1,3,5-triazin-2-yl)amino]carbonylamino)sulfonyl]benzoate of m.p. 129-134° C. (decomp.).

Example A8

Methyl 2-(diisobutylamino)-6-[([(4,6-dimethoxy-2-pyrimidinyl)amino]carbonyl-amino)sulfonyl]benzoate, sodium salt 0.2 g (0.382 mmol) of methyl 2-(diisobutylamino)-6-[([(4,6-dimethoxy-2-pyrimidinyl)amino]carbonylamino)sulfonyl]benzoate are stirred into 5 ml of tetrahydrofuran, and 0.04 g (416 µmol) of sodium tert-butoxide are then added. After 6 h, the solid that has been formed is filtered off with suction and dried. This gives 0.19 g (93% of theory) of methyl 2-(diisobutylamino)-6-[([(4,6-dimethoxy-2-pyrimidinyl)amino]carbonylamino)-6-sulfonyl]benzoate, sodium salt, as a colorless solid of m.p. 215-217° C.

The compounds described in Tables 1, 2 and 3 below are obtained in accordance with or similarly to Examples A1-A8 above.

Abbreviations in Tables 1, 2 and 3:

| m.p. = | melting point in ° C. |
|---|---|
| (decomp.) = | melting point with decomposition |
| Bu = | n-butyl; (correspondingly pentyl = n-pentyl, hexyl = n-hexyl) |
| Et = | ethyl |
| Me = | methyl |
| Ph = | phenyl |
| Pr, i-Pr, c-Pr = | n-propyl, isopropyl and cyclopropyl, respectively |

A diradical such as butylene of the formula

in the columns for $R^2$, $R^3$ means that $R^2$ and $R^3$ together are the diradical bridge and form a cyclic amine together with the nitrogen atom of the group $R^2R^3N$.

Het=heterocycle, where Het is one of the radicals T1 to T20

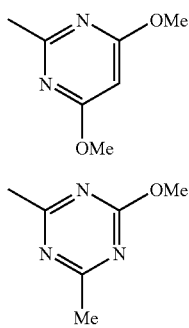

T1

T2

-continued

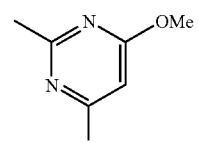

T3

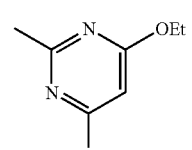

T4

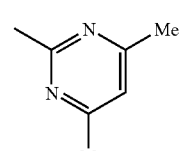

T5

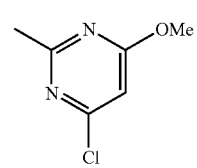

T6

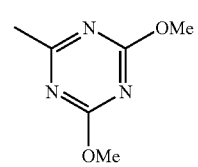

T7

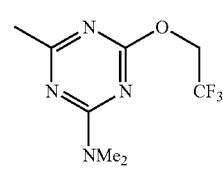

T8

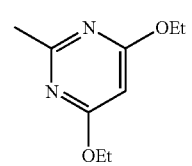

T9

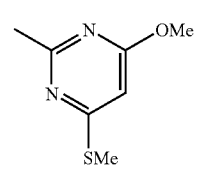

T10

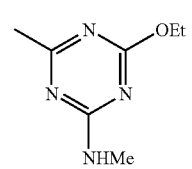

T11

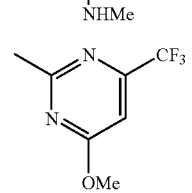

T12

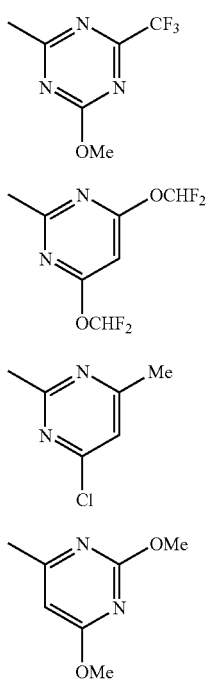
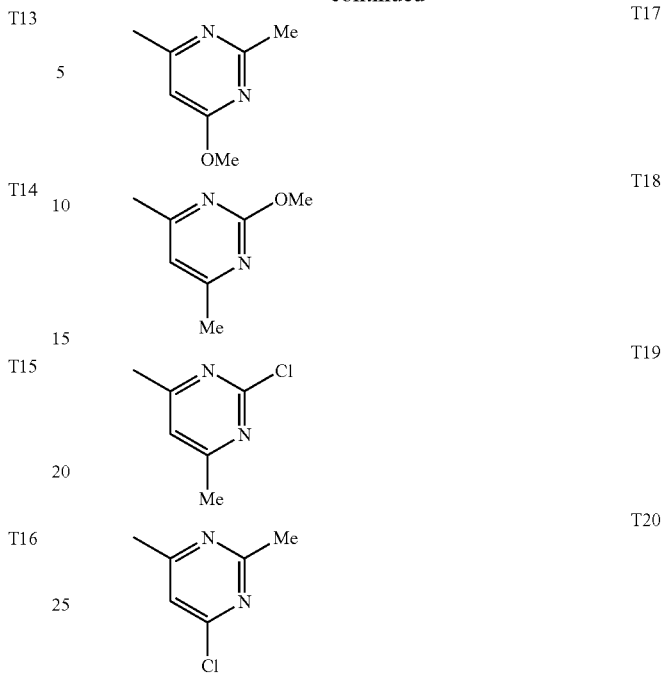
TABLE 1
Compounds of the formula (Ia)
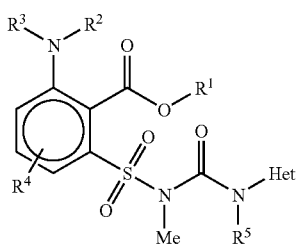
(Ia)
| Ex. No. | R¹ | R² | R³ | R⁴ | R⁵ | M | Het | m.p. |
|---|---|---|---|---|---|---|---|---|
| 1-1. | H | H | H | — | H | H | T1 | |
| 1-2. | H | H | H | — | H | Na | T1 | |
| 1-3. | H | H | H | — | H | H | T2 | |
| 1-4. | H | H | H | — | H | Na | T2 | |
| 1-5. | H | H | H | — | H | H | T5 | |
| 1-6. | H | H | H | — | H | Na | T5 | |
| 1-7. | H | H | H | — | H | H | T6 | |
| 1-8. | H | H | H | — | H | Na | T6 | |
| 1-9. | H | H | H | — | H | H | T7 | 141-142 |
| 1-10. | H | H | H | — | H | Na | T7 | |
| 1-11. | Me | H | H | — | H | H | T1 | 171-173 |
| 1-12. | Me | H | H | — | H | Na | T1 | |
| 1-13. | Me | H | H | — | Me | H | T2 | |
| 1-14. | Me | H | H | — | Me | Na | T2 | |
| 1-15. | Me | H | H | — | H | H | T2 | 126-127 (decomp.) |
| 1-16. | Me | H | H | — | H | Na | T2 | 239-242 |
| 1-17. | Me | H | H | — | H | H | T3 | 137-139 (decomp.) |
| 1-18. | Me | H | H | — | H | Na | T3 | |
| 1-19. | Me | H | H | — | H | H | T4 | |
| 1-20. | Me | H | H | — | H | Na | T4 | |
| 1-21. | Me | H | H | — | H | H | T5 | |
| 1-22. | Me | H | H | — | H | Na | T5 | |
| 1-23. | Me | H | H | — | H | H | T6 | 137-139 |
| 1-24. | Me | H | H | — | H | Na | T6 | |

TABLE 1-continued

Compounds of the formula (Ia)

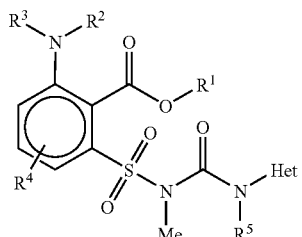

(Ia)

| Ex. No. | R¹ | R² | R³ | R⁴ | R⁵ | M | Het | m.p. |
|---|---|---|---|---|---|---|---|---|
| 1-25. | Me | H | H | — | H | H | T7 | 129-134 (decomp.) |
| 1-26. | Me | H | H | — | H | Na | T7 | 257-260 (decomp.) |
| 1-27. | Me | H | H | — | Me | H | T7 | |
| 1-28. | Me | H | H | — | Me | Na | T7 | |
| 1-29. | Me | H | H | — | H | H | T8 | |
| 1-30. | Me | H | H | — | H | Na | T8 | |
| 1-31. | Me | H | H | — | H | H | T9 | |
| 1-32. | Me | H | H | — | H | Na | T9 | |
| 1-33. | Me | H | H | — | H | H | T10 | |
| 1-34. | Me | H | H | — | H | Na | T10 | |
| 1-35. | Me | H | H | — | H | H | T11 | |
| 1-36. | Me | H | H | — | H | Na | T11 | |
| 1-37. | Me | H | H | — | H | H | T12 | |
| 1-38. | Me | H | H | — | H | Na | T12 | |
| 1-39. | Me | H | H | — | H | H | T13 | |
| 1-40. | Me | H | H | — | H | Na | T13 | |
| 1-41. | Me | H | H | — | H | H | T14 | 162-164 (decomp.) |
| 1-42. | Me | H | H | — | H | Na | T14 | |
| 1-43. | Me | H | H | — | H | H | T15 | |
| 1-44. | Me | H | H | — | H | Na | T15 | |
| 1-45. | Et | H | H | — | H | H | T1 | 164-166 |
| 1-46. | Et | H | H | — | H | Na | T1 | |
| 1-47. | Et | H | H | — | H | H | T2 | 149-151 |
| 1-48. | Et | H | H | — | H | Na | T2 | |
| 1-49. | Et | H | H | — | H | H | T3 | |
| 1-50. | Et | H | H | — | H | Na | T3 | |
| 1-51. | Et | H | H | — | H | H | T4 | |
| 1-52. | Et | H | H | — | H | Na | T4 | |
| 1-53. | Et | H | H | — | H | H | T5 | |
| 1-54. | Et | H | H | — | H | Na | T5 | |
| 1-55. | Et | H | H | — | H | H | T6 | 157-158 |
| 1-56. | Et | H | H | — | H | Na | T6 | |
| 1-57. | Et | H | H | — | H | H | T7 | 158-160 |
| 1-58. | Et | H | H | — | H | Na | T7 | |
| 1-59. | Et | H | H | — | H | H | T8 | |
| 1-60. | Et | H | H | — | H | Na | T8 | |
| 1-61. | Et | H | H | — | H | H | T9 | |
| 1-62. | Et | H | H | — | H | Na | T9 | |
| 1-63. | Et | H | H | — | H | H | T10 | |
| 1-64. | Et | H | H | — | H | Na | T10 | |
| 1-65. | Et | H | H | — | H | H | T11 | |
| 1-66. | Et | H | H | — | H | Na | T11 | |
| 1-67. | Et | H | H | — | H | H | T12 | |
| 1-68. | Et | H | H | — | H | Na | T12 | |
| 1-69. | Et | H | H | — | H | H | T13 | |
| 1-70. | Et | H | H | — | H | Na | T13 | |
| 1-71. | Et | H | H | — | H | H | T14 | |
| 1-72. | Et | H | H | — | H | Na | T14 | |
| 1-73. | Et | H | H | — | H | H | T15 | |
| 1-74. | Et | H | H | — | H | Na | T15 | |
| 1-75. | i-Pr | H | H | — | H | H | T1 | |
| 1-76. | i-Pr | H | H | — | H | Na | T1 | |
| 1-77. | i-Pr | H | H | — | H | H | T2 | |
| 1-78. | i-Pr | H | H | — | H | Na | T2 | |
| 1-79. | i-Pr | H | H | — | H | H | T5 | |
| 1-80. | i-Pr | H | H | — | H | Na | T5 | |
| 1-81. | i-Pr | H | H | — | H | H | T6 | |
| 1-82. | i-Pr | H | H | — | H | Na | T6 | |
| 1-83. | i-Pr | H | H | — | H | H | T7 | |
| 1-84. | i-Pr | H | H | — | H | Na | T7 | |
| 1-85. | Allyl | H | H | — | H | H | T1 | |

TABLE 1-continued

Compounds of the formula (Ia)

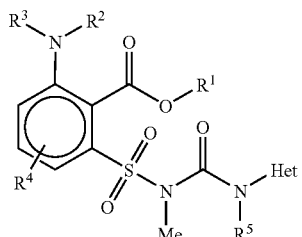

(Ia)

| Ex. No. | R¹ | R² | R³ | R⁴ | R⁵ | M | Het | m.p. |
|---|---|---|---|---|---|---|---|---|
| 1-86. | Allyl | H | H | — | H | Na | T1 | |
| 1-87. | Allyl | H | H | — | H | H | T2 | |
| 1-88. | Allyl | H | H | — | H | Na | T2 | |
| 1-89. | Allyl | H | H | — | H | H | T5 | |
| 1-90. | Allyl | H | H | — | H | Na | T5 | |
| 1-91. | Allyl | H | H | — | H | H | T6 | |
| 1-92. | Allyl | H | H | — | H | Na | T6 | |
| 1-93. | Allyl | H | H | — | H | H | T7 | |
| 1-94. | Allyl | H | H | — | H | Na | T7 | |
| 1-95. | 3-Oxetanyl | H | H | — | H | H | T1 | |
| 1-96. | 3-Oxetanyl | H | H | — | H | Na | T1 | |
| 1-97. | 3-Oxetanyl | H | H | — | H | H | T2 | |
| 1-98. | 3-Oxetanyl | H | H | — | H | Na | T2 | |
| 1-99. | 3-Oxetanyl | H | H | — | H | H | T5 | |
| 1-100. | 3-Oxetanyl | H | H | — | H | Na | T5 | |
| 1-101. | 3-Oxetanyl | H | H | — | H | H | T6 | |
| 1-102. | 3-Oxetanyl | H | H | — | H | Na | T6 | |
| 1-103. | 3-Oxetanyl | H | H | — | H | H | T7 | |
| 1-104. | 3-Oxetanyl | H | H | — | H | Na | T7 | |
| 1-105. | Me | Me | H | — | H | H | T1 | 169-171 |
| 1-106. | Me | Me | H | — | H | Na | T1 | |
| 1-107. | Me | Me | H | — | H | H | T2 | |
| 1-108. | Me | Me | H | — | H | Na | T2 | |
| 1-109. | Me | Me | H | — | H | H | T6 | |
| 1-110. | Me | Me | H | — | H | Na | T6 | |
| 1-111. | Me | Me | H | — | H | H | T7 | |
| 1-112. | Me | Me | H | — | H | Na | T7 | |
| 1-113. | Et | Me | H | — | H | H | T1 | |
| 1-114. | Et | Me | H | — | H | Na | T1 | |
| 1-115. | Et | Me | H | — | H | H | T2 | |
| 1-116. | Et | Me | H | — | H | Na | T2 | |
| 1-117. | i-Pr | Me | H | — | H | H | T1 | |
| 1-118. | i-Pr | Me | H | — | H | Na | T1 | |
| 1-119. | i-Pr | Me | H | — | H | H | T2 | |
| 1-120. | i-Pr | Me | H | — | H | Na | T2 | |
| 1-121. | Allyl | Me | H | — | H | H | T1 | |
| 1-122. | Allyl | Me | H | — | H | Na | T1 | |
| 1-123. | Allyl | Me | H | — | H | H | T2 | |
| 1-124. | Allyl | Me | H | — | H | Na | T2 | |
| 1-125. | 3-Oxetanyl | Me | H | — | H | H | T1 | |
| 1-126. | 3-Oxetanyl | Me | H | — | H | Na | T1 | |
| 1-127. | 3-Oxetanyl | Me | H | — | H | H | T2 | |
| 1-128. | 3-Oxetanyl | Me | H | — | H | Na | T2 | |
| 1-129. | Me | Et | H | — | H | H | T1 | 164-166 |
| 1-130. | Me | Et | H | — | H | Na | T1 | |
| 1-131. | Me | Et | H | — | H | H | T2 | 215-217 |
| 1-132. | Me | Et | H | — | H | Na | T2 | |
| 1-133. | Me | Et | H | — | H | H | T6 | |
| 1-134. | Me | Et | H | — | H | Na | T6 | |
| 1-135. | Me | Et | H | — | H | H | T7 | 170-172 |
| 1-136. | Me | Et | H | — | H | Na | T7 | |
| 1-137. | Et | Et | H | — | H | H | T1 | |
| 1-138. | Et | Et | H | — | H | Na | T1 | |
| 1-139. | Et | Et | H | — | H | H | T2 | |
| 1-140. | Et | Et | H | — | H | Na | T2 | |
| 1-141. | i-Pr | Et | H | — | H | H | T1 | |
| 1-142. | i-Pr | Et | H | — | H | Na | T1 | |
| 1-143. | i-Pr | Et | H | — | H | H | T2 | |
| 1-144. | i-Pr | Et | H | — | H | Na | T2 | |
| 1-145. | Allyl | Et | H | — | H | H | T1 | |
| 1-146. | Allyl | Et | H | — | H | Na | T1 | |

TABLE 1-continued

Compounds of the formula (Ia)

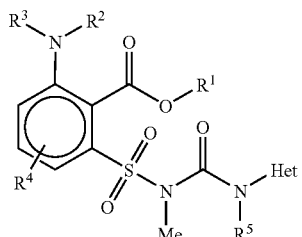

(Ia)

| Ex. No. | R¹ | R² | R³ | R⁴ | R⁵ | M | Het | m.p. |
|---|---|---|---|---|---|---|---|---|
| 1-147. | Allyl | Et | H | — | H | H | T2 | |
| 1-148. | Allyl | Et | H | — | H | Na | T2 | |
| 1-149. | 3-Oxetanyl | Et | H | — | H | H | T1 | |
| 1-150. | 3-Oxetanyl | Et | H | — | H | Na | T1 | |
| 1-151. | 3-Oxetanyl | Et | H | — | H | H | T2 | |
| 1-152. | 3-Oxetanyl | Et | H | — | H | Na | T2 | |
| 1-153. | Me | i-Pr | H | — | H | H | T1 | 165-167 |
| 1-154. | Me | i-Pr | H | — | H | Na | T1 | 124-126 |
| 1-155. | Me | i-Pr | H | — | H | H | T2 | 139-140 (decomp.) |
| 1-156. | Me | i-Pr | H | — | H | Na | T2 | |
| 1-157. | Me | i-Pr | H | — | H | H | T6 | |
| 1-158. | Me | i-Pr | H | — | H | Na | T6 | |
| 1-159. | Me | i-Pr | H | — | H | H | T7 | 161-163 (decomp.) |
| 1-160. | Me | i-Pr | H | — | H | Na | T7 | |
| 1-161. | Et | i-Pr | H | — | H | H | T1 | |
| 1-162. | Et | i-Pr | H | — | H | Na | T1 | |
| 1-163. | Et | i-Pr | H | — | H | H | T2 | |
| 1-164. | Et | i-Pr | H | — | H | Na | T2 | |
| 1-165. | i-Pr | i-Pr | H | — | H | H | T1 | |
| 1-166. | i-Pr | i-Pr | H | — | H | Na | T1 | |
| 1-167. | i-Pr | i-Pr | H | — | H | H | T2 | |
| 1-168. | i-Pr | i-Pr | H | — | H | Na | T2 | |
| 1-169. | Allyl | i-Pr | H | — | H | H | T1 | |
| 1-170. | Allyl | i-Pr | H | — | H | Na | T1 | |
| 1-171. | Allyl | i-Pr | H | — | H | H | T2 | |
| 1-172. | Allyl | i-Pr | H | — | H | Na | T2 | |
| 1-173. | 3-Oxetanyl | i-Pr | H | — | H | H | T1 | |
| 1-174. | 3-Oxetanyl | i-Pr | H | — | H | Na | T1 | |
| 1-175. | 3-Oxetanyl | i-Pr | H | — | H | H | T2 | |
| 1-176. | 3-Oxetanyl | i-Pr | H | — | H | Na | T2 | |
| 1-177. | Me | CH₂i-Pr | H | — | H | H | T1 | 163-165 |
| 1-178. | Me | CH₂i-Pr | H | — | H | Na | T1 | |
| 1-179. | Me | CH₂i-Pr | H | — | H | H | T2 | 171-173 (decomp.) |
| 1-180. | Me | CH₂i-Pr | H | — | H | Na | T2 | |
| 1-181. | Me | CH₂i-Pr | H | — | H | H | T6 | |
| 1-182. | Me | CH₂i-Pr | H | — | H | Na | T6 | |
| 1-183. | Me | CH₂i-Pr | H | — | H | H | T7 | 174-176 (decomp.) |
| 1-184. | Me | CH₂i-Pr | H | — | H | Na | T7 | |
| 1-185. | Et | CH₂i-Pr | H | — | H | H | T1 | |
| 1-186. | Et | CH₂i-Pr | H | — | H | Na | T1 | |
| 1-187. | Et | CH₂i-Pr | H | — | H | H | T2 | |
| 1-188. | Et | CH₂i-Pr | H | — | H | Na | T2 | |
| 1-189. | Et | CH₂i-Pr | H | — | H | H | T6 | |
| 1-190. | Et | CH₂i-Pr | H | — | H | Na | T6 | |
| 1-191. | Et | CH₂i-Pr | H | — | H | H | T7 | |
| 1-192. | Et | CH₂i-Pr | H | — | H | Na | T7 | |
| 1-193. | i-Pr | CH₂i-Pr | H | — | H | H | T1 | |
| 1-194. | i-Pr | CH₂i-Pr | H | — | H | Na | T1 | |
| 1-195. | i-Pr | CH₂i-Pr | H | — | H | H | T2 | |
| 1-196. | i-Pr | CH₂i-Pr | H | — | H | Na | T2 | |
| 1-197. | Allyl | CH₂i-Pr | H | — | H | H | T1 | |
| 1-198. | Allyl | CH₂i-Pr | H | — | H | Na | T1 | |
| 1-199. | Allyl | CH₂i-Pr | H | — | H | H | T2 | |
| 1-200. | Allyl | CH₂i-Pr | H | — | H | Na | T2 | |
| 1-201. | 3-Oxetanyl | CH₂i-Pr | H | — | H | H | T1 | |
| 1-202. | 3-Oxetanyl | CH₂i-Pr | H | — | H | Na | T1 | |
| 1-203. | 3-Oxetanyl | CH₂i-Pr | H | — | H | H | T2 | |
| 1-204. | 3-Oxetanyl | CH₂i-Pr | H | — | H | Na | T2 | |
| 1-205. | Me | CH₂CH₂F | H | — | H | H | T1 | |
| 1-206. | Me | CH₂CH₂F | H | — | H | Na | T1 | |
| 1-207. | Me | CH₂CH₂F | H | — | H | H | T2 | |

TABLE 1-continued

Compounds of the formula (Ia)

| Ex. No. | R$^1$ | R$^2$ | R$^3$ | R$^4$ | R$^5$ | M | Het | m.p. |
|---|---|---|---|---|---|---|---|---|
| 1-208. | Me | CH$_2$CH$_2$F | H | — | H | Na | T2 | |
| 1-209. | Me | CH$_2$CH$_2$F | H | — | H | H | T6 | |
| 1-210. | Me | CH$_2$CH$_2$F | H | — | H | Na | T6 | |
| 1-211. | Me | CH$_2$CH$_2$F | H | — | H | H | T7 | |
| 1-212. | Me | CH$_2$CH$_2$F | H | — | H | Na | T7 | |
| 1-213. | Et | CH$_2$CH$_2$F | H | — | H | H | T1 | |
| 1-214. | Et | CH$_2$CH$_2$F | H | — | H | Na | T1 | |
| 1-215. | Et | CH$_2$CH$_2$F | H | — | H | H | T2 | |
| 1-216. | Et | CH$_2$CH$_2$F | H | — | H | Na | T2 | |
| 1-217. | Et | CH$_2$CH$_2$F | H | — | H | H | T6 | |
| 1-218. | Et | CH$_2$CH$_2$F | H | — | H | Na | T6 | |
| 1-219. | Et | CH$_2$CH$_2$F | H | — | H | H | T7 | |
| 1-220. | Et | CH$_2$CH$_2$F | H | — | H | Na | T7 | |
| 1-221. | i-Pr | CH$_2$CH$_2$F | H | — | H | H | T1 | |
| 1-222. | i-Pr | CH$_2$CH$_2$F | H | — | H | Na | T1 | |
| 1-223. | i-Pr | CH$_2$CH$_2$F | H | — | H | H | T2 | |
| 1-224. | i-Pr | CH$_2$CH$_2$F | H | — | H | Na | T2 | |
| 1-225. | Allyl | CH$_2$CH$_2$F | H | — | H | H | T1 | |
| 1-226. | Allyl | CH$_2$CH$_2$F | H | — | H | Na | T1 | |
| 1-227. | Allyl | CH$_2$CH$_2$F | H | — | H | H | T2 | |
| 1-228. | Allyl | CH$_2$CH$_2$F | H | — | H | Na | T2 | |
| 1-229. | 3-Oxetanyl | CH$_2$CH$_2$F | H | — | H | H | T1 | |
| 1-230. | 3-Oxetanyl | CH$_2$CH$_2$F | H | — | H | Na | T1 | |
| 1-231. | 3-Oxetanyl | CH$_2$CH$_2$F | H | — | H | H | T2 | |
| 1-232. | 3-Oxetanyl | CH$_2$CH$_2$F | H | — | H | Na | T2 | |
| 1-233. | Me | CH$_2$CH$_2$CF$_3$ | H | — | H | H | T1 | |
| 1-234. | Me | CH$_2$CH$_2$CF$_3$ | H | — | H | Na | T1 | |
| 1-235. | Me | CH$_2$CH$_2$CF$_3$ | H | — | H | H | T2 | |
| 1-236. | Me | CH$_2$CH$_2$CF$_3$ | H | — | H | Na | T2 | |
| 1-237. | Me | CH$_2$CH$_2$CF$_3$ | H | — | H | H | T6 | |
| 1-238. | Me | CH$_2$CH$_2$CF$_3$ | H | — | H | Na | T6 | |
| 1-239. | Me | CH$_2$CH$_2$CF$_3$ | H | — | H | H | T7 | |
| 1-240. | Me | CH$_2$CH$_2$CF$_3$ | H | — | H | Na | T7 | |
| 1-241. | Me | CH$_2$CH$_2$CH$_2$CF$_3$ | H | — | H | H | T1 | 173-175 |
| 1-242. | Me | CH$_2$CH$_2$CH$_2$CF$_3$ | H | — | H | Na | T1 | |
| 1-243. | Me | CH$_2$CH$_2$CH$_2$CF$_3$ | H | — | H | H | T2 | 177-179 |
| 1-244. | Me | CH$_2$CH$_2$CH$_2$CF$_3$ | H | — | H | Na | T2 | |
| 1-245. | Me | CH$_2$CH$_2$CH$_2$CF$_3$ | H | — | H | H | T6 | |
| 1-246. | Me | CH$_2$CH$_2$CH$_2$CF$_3$ | H | — | H | Na | T6 | |
| 1-247. | Me | CH$_2$CH$_2$CH$_2$CF$_3$ | H | — | H | H | T7 | 171-173 |
| 1-248. | Me | CH$_2$CH$_2$CH$_2$CF$_3$ | H | — | H | Na | T7 | |
| 1-249. | Me | CH(Me)CH$_2$C(O)OMe | H | — | H | H | T1 | |
| 1-250. | Me | CH(Me)CH$_2$C(O)OMe | H | — | H | Na | T1 | |
| 1-251. | Me | CH(Me)CH$_2$C(O)OMe | H | — | H | H | T2 | |
| 1-252. | Me | CH(Me)CH$_2$C(O)OMe | H | — | H | Na | T2 | |
| 1-253. | Me | CH(Me)CH$_2$C(O)OMe | H | — | H | H | T6 | |
| 1-254. | Me | CH(Me)CH$_2$C(O)OMe | H | — | H | Na | T6 | |
| 1-255. | Me | CH(Me)CH$_2$C(O)OMe | H | — | H | H | T7 | |
| 1-256. | Me | CH(Me)CH$_2$C(O)OMe | H | — | H | Na | T7 | |
| 1-257. | Me | CH(Me)CH$_2$C(O)NH$_2$ | H | — | H | H | T1 | |
| 1-258. | Me | CH(Me)CH$_2$C(O)NH$_2$ | H | — | H | Na | T1 | |
| 1-259. | Me | CH(Me)CH$_2$C(O)NH$_2$ | H | — | H | H | T2 | |
| 1-260. | Me | CH(Me)CH$_2$C(O)NH$_2$ | H | — | H | Na | T2 | |
| 1-261. | Me | CH(Me)CH$_2$C(O)NH$_2$ | H | — | H | H | T6 | |
| 1-262. | Me | CH(Me)CH$_2$C(O)NH$_2$ | H | — | H | Na | T6 | |
| 1-263. | Me | CH(Me)CH$_2$C(O)NH$_2$ | H | — | H | H | T7 | |
| 1-264. | Me | CH(Me)CH$_2$C(O)NH$_2$ | H | — | H | Na | T7 | |
| 1-265. | Me | CH(Me)CH$_2$CH$_3$ | H | — | H | H | T1 | 171-173 |
| 1-266. | Me | CH(Me)CH$_2$CH$_3$ | H | — | H | Na | T1 | |
| 1-267. | Me | CH(Me)CH$_2$CH$_3$ | H | — | H | H | T2 | 154-156 |
| 1-268. | Me | CH(Me)CH$_2$CH$_3$ | H | — | H | Na | T2 | |

TABLE 1-continued

Compounds of the formula (Ia)

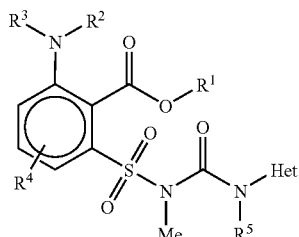

| Ex. No. | R$^1$ | R$^2$ | R$^3$ | R$^4$ | R$^5$ | M | Het | m.p. |
|---|---|---|---|---|---|---|---|---|
| 1-269. | Me | CH(Me)CH$_2$CH$_3$ | H | — | H | H | T6 | |
| 1-270. | Me | CH(Me)CH$_2$CH$_3$ | H | — | H | Na | T6 | |
| 1-271. | Me | CH(Me)CH$_2$CH$_3$ | H | — | H | H | T7 | 172-174 |
| 1-272. | Me | CH(Me)CH$_2$CH$_3$ | H | — | H | Na | T7 | |
| 1-273. | Me | Allyl | H | — | H | H | T1 | |
| 1-274. | Me | Allyl | H | — | H | Na | T1 | |
| 1-275. | Me | Allyl | H | — | H | H | T2 | |
| 1-276. | Me | Allyl | H | — | H | Na | T2 | |
| 1-277. | Me | Allyl | H | — | H | H | T6 | |
| 1-278. | Me | Allyl | H | — | H | Na | T6 | |
| 1-279. | Me | Allyl | H | — | H | H | T7 | |
| 1-280. | Me | Allyl | H | — | H | Na | T7 | |
| 1-281. | Et | Allyl | H | — | H | H | T1 | |
| 1-282. | Et | Allyl | H | — | H | Na | T1 | |
| 1-283. | Et | Allyl | H | — | H | H | T2 | |
| 1-284. | Et | Allyl | H | — | H | Na | T2 | |
| 1-285. | Et | Allyl | H | — | H | H | T6 | |
| 1-286. | Et | Allyl | H | — | H | Na | T6 | |
| 1-287. | Et | Allyl | H | — | H | H | T7 | |
| 1-288. | Et | Allyl | H | — | H | Na | T7 | |
| 1-289. | i-Pr | Allyl | H | — | H | H | T1 | |
| 1-290. | i-Pr | Allyl | H | — | H | Na | T1 | |
| 1-291. | i-Pr | Allyl | H | — | H | H | T2 | |
| 1-292. | i-Pr | Allyl | H | — | H | Na | T2 | |
| 1-293. | Allyl | Allyl | H | — | H | H | T1 | |
| 1-294. | Allyl | Allyl | H | — | H | Na | T1 | |
| 1-295. | Allyl | Allyl | H | — | H | H | T2 | |
| 1-296. | Allyl | Allyl | H | — | H | Na | T2 | |
| 1-297. | 3-Oxetanyl | Allyl | H | — | H | H | T1 | |
| 1-298. | 3-Oxetanyl | Allyl | H | — | H | Na | T1 | |
| 1-299. | 3-Oxetanyl | Allyl | H | — | H | H | T2 | |
| 1-300. | 3-Oxetanyl | Allyl | H | — | H | Na | T2 | |
| 1-301. | Me | Propargyl | H | — | H | H | T1 | |
| 1-302. | Me | Propargyl | H | — | H | Na | T1 | |
| 1-303. | Me | Propargyl | H | — | H | H | T2 | |
| 1-304. | Me | Propargyl | H | — | H | Na | T2 | |
| 1-305. | Me | Propargyl | H | — | H | H | T6 | |
| 1-306. | Me | Propargyl | H | — | H | Na | T6 | |
| 1-307. | Me | Propargyl | H | — | H | H | T7 | |
| 1-308. | Me | Propargyl | H | — | H | Na | T7 | |
| 1-309. | Et | Propargyl | H | — | H | H | T1 | |
| 1-310. | Et | Propargyl | H | — | H | Na | T1 | |
| 1-311. | Et | Propargyl | H | — | H | H | T2 | |
| 1-312. | Et | Propargyl | H | — | H | Na | T2 | |
| 1-313. | Et | Propargyl | H | — | H | H | T6 | |
| 1-314. | Et | Propargyl | H | — | H | Na | T6 | |
| 1-315. | Et | Propargyl | H | — | H | H | T7 | |
| 1-316. | Et | Propargyl | H | — | H | Na | T7 | |
| 1-317. | i-Pr | Propargyl | H | — | H | H | T1 | |
| 1-318. | i-Pr | Propargyl | H | — | H | Na | T1 | |
| 1-319. | i-Pr | Propargyl | H | — | H | H | T2 | |
| 1-320. | i-Pr | Propargyl | H | — | H | Na | T2 | |
| 1-321. | Allyl | Propargyl | H | — | H | H | T1 | |
| 1-322. | Allyl | Propargyl | H | — | H | Na | T1 | |
| 1-323. | Allyl | Propargyl | H | — | H | H | T2 | |
| 1-324. | Allyl | Propargyl | H | — | H | Na | T2 | |
| 1-325. | 3-Oxetanyl | Propargyl | H | — | H | H | T1 | |
| 1-326. | 3-Oxetanyl | Propargyl | H | — | H | Na | T1 | |
| 1-327. | 3-Oxetanyl | Propargyl | H | — | H | H | T2 | |
| 1-328. | 3-Oxetanyl | Propargyl | H | — | H | Na | T2 | |
| 1-329. | Me | OMe | H | — | H | H | T1 | |

TABLE 1-continued

Compounds of the formula (Ia)

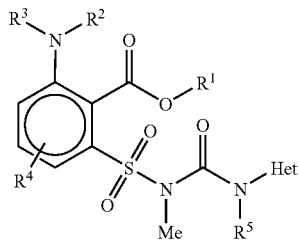

| Ex. No. | R¹ | R² | R³ | R⁴ | R⁵ | M | Het | m.p. |
|---|---|---|---|---|---|---|---|---|
| 1-330. | Me | OMe | H | — | H | Na | T1 | |
| 1-331. | Me | OMe | H | — | H | H | T2 | |
| 1-332. | Me | OMe | H | — | H | Na | T2 | |
| 1-333. | Me | OMe | H | — | H | H | T6 | |
| 1-334. | Me | OMe | H | — | H | Na | T6 | |
| 1-335. | Me | OMe | H | — | H | H | T7 | |
| 1-336. | Me | OMe | H | — | H | Na | T7 | |
| 1-337. | Et | OMe | H | — | H | H | T1 | |
| 1-338. | Et | OMe | H | — | H | Na | T1 | |
| 1-339. | Et | OMe | H | — | H | H | T2 | |
| 1-340. | Et | OMe | H | — | H | Na | T2 | |
| 1-341. | Et | OMe | H | — | H | H | T6 | |
| 1-342. | Et | OMe | H | — | H | Na | T6 | |
| 1-343. | Et | OMe | H | — | H | H | T7 | |
| 1-344. | Et | OMe | H | — | H | Na | T7 | |
| 1-345. | i-Pr | OMe | H | — | H | H | T1 | |
| 1-346. | i-Pr | OMe | H | — | H | Na | T1 | |
| 1-347. | i-Pr | OMe | H | — | H | H | T2 | |
| 1-348. | i-Pr | OMe | H | — | H | Na | T2 | |
| 1-349. | Allyl | OMe | H | — | H | H | T1 | |
| 1-350. | Allyl | OMe | H | — | H | Na | T1 | |
| 1-351. | Allyl | OMe | H | — | H | H | T2 | |
| 1-352. | Allyl | OMe | H | — | H | Na | T2 | |
| 1-353. | Me | c-Pr | H | — | H | H | T1 | 148-150 (decomp.) |
| 1-354. | Me | c-Pr | H | — | H | Na | T1 | |
| 1-355. | Me | c-Pr | H | — | H | H | T2 | 147-149 |
| 1-356. | Me | c-Pr | H | — | H | Na | T2 | |
| 1-357. | Me | c-Pr | H | — | H | H | T6 | |
| 1-358. | Me | c-Pr | H | — | H | Na | T6 | |
| 1-359. | Me | c-Pr | H | — | H | H | T7 | 177-179 |
| 1-360. | Me | c-Pr | H | — | H | Na | T7 | |
| 1-361. | 3-Oxetanyl | OMe | H | — | H | H | T1 | |
| 1-362. | 3-Oxetanyl | OMe | H | — | H | Na | T1 | |
| 1-363. | 3-Oxetanyl | OMe | H | — | H | H | T2 | |
| 1-364. | 3-Oxetanyl | OMe | H | — | H | Na | T2 | |
| 1-365. | Me | NMe₂ | H | — | H | H | T1 | |
| 1-366. | Me | NMe₂ | H | — | H | Na | T1 | |
| 1-367. | Me | NMe₂ | H | — | H | H | T2 | |
| 1-368. | Me | NMe₂ | H | — | H | Na | T2 | |
| 1-369. | Me | NHCHO | H | — | H | H | T1 | |
| 1-370. | Me | NHCHO | H | — | H | Na | T1 | |
| 1-371. | Me | NHCHO | H | — | H | H | T2 | |
| 1-372. | Me | NHCHO | H | — | H | Na | T2 | |
| 1-373. | Me | NHC(O)Me | H | — | H | H | T1 | |
| 1-374. | Me | NHC(O)Me | H | — | H | Na | T1 | |
| 1-375. | Me | NHC(O)Me | H | — | H | H | T2 | |
| 1-376. | Me | NHC(O)Me | H | — | H | Na | T2 | |
| 1-377. | Me | NHSO₂Me | H | — | H | H | T1 | |
| 1-378. | Me | NHSO₂Me | H | — | H | Na | T1 | |
| 1-379. | Me | NHSO₂Me | H | — | H | H | T2 | |
| 1-380. | Me | NHSO₂Me | H | — | H | Na | T2 | |
| 1-381. | Me | CH₂Ph | H | — | H | H | T1 | 189-191 |
| 1-382. | Me | CH₂Ph | H | — | H | Na | T1 | |
| 1-383. | Me | CH₂Ph | H | — | H | H | T2 | 151-153 |
| 1-384. | Me | CH₂Ph | H | — | H | Na | T2 | |
| 1-385. | Me | CH₂Ph | H | — | H | H | T6 | |
| 1-386. | Me | CH₂Ph | H | — | H | Na | T6 | |
| 1-387. | Me | CH₂Ph | H | — | H | H | T7 | 166-168 (decomp.) |
| 1-388. | Me | CH₂Ph | H | — | H | Na | T7 | |
| 1-389. | Me | CH₂OMe | H | — | H | H | T1 | |
| 1-390. | Me | CH₂OMe | H | — | H | Na | T1 | |

TABLE 1-continued

Compounds of the formula (Ia)

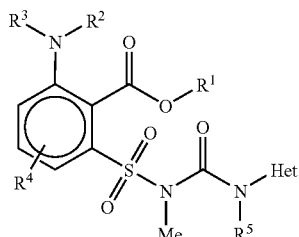

(Ia)

| Ex. No. | R¹ | R² | R³ | R⁴ | R⁵ | M | Het | m.p. |
|---|---|---|---|---|---|---|---|---|
| 1-391. | Me | CH₂OMe | H | — | H | H | T2 | |
| 1-392. | Me | CH₂OMe | H | — | H | Na | T2 | |
| 1-393. | Me | CH₂C(O)Me | H | — | H | H | T1 | |
| 1-394. | Me | CH₂C(O)Me | H | — | H | Na | T1 | |
| 1-395. | Me | CH₂C(O)Me | H | — | H | H | T2 | |
| 1-396. | Me | CH₂C(O)Me | H | — | H | Na | T2 | |
| 1-397. | Me | CH₂C(O)OMe | H | — | H | H | T1 | |
| 1-398. | Me | CH₂C(O)OMe | H | — | H | Na | T1 | |
| 1-399. | Me | CH₂C(O)OMe | H | — | H | H | T2 | |
| 1-400. | Me | CH₂C(O)OMe | H | — | H | Na | T2 | |
| 1-401. | Me | Me | Me | — | H | H | T1 | 194-196 |
| 1-402. | Me | Me | Me | — | H | Na | T1 | |
| 1-403. | Me | Me | Me | — | H | H | T2 | |
| 1-404. | Me | Me | Me | — | H | Na | T2 | |
| 1-405. | Me | Me | Me | — | H | H | T6 | |
| 1-406. | Me | Me | Me | — | H | Na | T6 | |
| 1-407. | Me | Me | Me | — | H | H | T7 | |
| 1-408. | Me | Me | Me | — | H | Na | T7 | |
| 1-409. | Me | Me | Et | — | H | H | T1 | |
| 1-410. | Me | Me | Et | — | H | Na | T1 | |
| 1-411. | Me | Me | Et | — | H | H | T2 | |
| 1-412. | Me | Me | Et | — | H | Na | T2 | |
| 1-413. | Me | Me | i-Pr | — | H | H | T1 | |
| 1-414. | Me | Me | i-Pr | — | H | Na | T1 | |
| 1-415. | Me | Me | i-Pr | — | H | H | T2 | |
| 1-416. | Me | Me | i-Pr | — | H | Na | T2 | |
| 1-417. | Me | Et | Et | — | H | H | T1 | 207-209 |
| 1-418. | Me | Et | Et | — | H | Na | T1 | |
| 1-419. | Me | Et | Et | — | H | H | T2 | |
| 1-420. | Me | Et | Et | — | H | Na | T2 | |
| 1-421. | Me | i-Pr | i-Pr | — | H | H | T1 | |
| 1-422. | Me | i-Pr | i-Pr | — | H | Na | T1 | |
| 1-423. | Me | i-Pr | i-Pr | — | H | H | T2 | |
| 1-424. | Me | i-Pr | i-Pr | — | H | Na | T2 | |
| 1-425. | Me | CH₂i-Pr | CH₂i-Pr | — | H | H | T1 | 166-167 |
| 1-426. | Me | CH₂i-Pr | CH₂i-Pr | — | H | Na | T1 | 215-217 |
| 1-427. | Me | CH₂i-Pr | CH₂i-Pr | — | H | H | T2 | |
| 1-428. | Me | CH₂i-Pr | CH₂i-Pr | — | H | Na | T2 | |
| 1-429. | Me |  | | — | H | H | T1 | |
| 1-430. | Me |  | | — | H | Na | T1 | |
| 1-431. | Me |  | | — | H | H | T2 | |
| 1-432. | Me |  | | — | H | Na | T2 | |
| 1-433. | Me |  | | — | H | H | T1 | 216-218 |

TABLE 1-continued
Compounds of the formula (Ia)
(Ia)
| Ex. No. | R¹ | R² | R³ | R⁴ | R⁵ | M | Het | m.p. |
|---|---|---|---|---|---|---|---|---|
| 1-434. | Me |  | | — | H | Na | T1 | |
| 1-435. | Me |  | | — | H | H | T2 | 193-195 |
| 1-436. | Me |  | | — | H | Na | T2 | |
| 1-437. | Me |  | | — | H | H | T6 | |
| 1-438. | Me |  | | — | H | Na | T6 | |
| 1-439. | Me |  | | — | H | H | T7 | 200-202 |
| 1-440. | Me |  | | — | H | Na | T7 | |
| 1-441. | Me |  | | — | H | H | T1 | |
| 1-442. | Me |  | | — | H | Na | T1 | |
| 1-443. | Me |  | | — | H | H | T2 | |
| 1-444. | Me |  | | — | H | Na | T2 | |
| 1-445. | Me |  | | — | H | H | T1 | |
| 1-446. | Me |  | | — | H | Na | T1 | |

TABLE 1-continued
Compounds of the formula (Ia)
| Ex. No. | R¹ | R² | R³ | R⁴ | R⁵ | M | Het | m.p. |
|---|---|---|---|---|---|---|---|---|
| 1-447. | Me |  | | — | H | H | T2 | |
| 1-448. | Me |  | | — | H | Na | T2 | |
| 1-449. | Me |  | | — | H | H | T1 | |
| 1-450. | Me |  | | — | H | Na | T1 | |
| 1-451. | Me |  | | — | H | H | T2 | |
| 1-452. | Me | 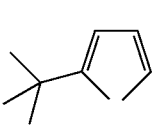 | | — | H | Na | T2 | |
| 1-453. | Me | 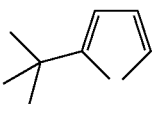 | | — | H | H | T1 | 211-213 (decomp.) |
| 1-454. | Me | 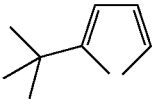 | | — | H | Na | T1 | |
| 1-455. | Me | 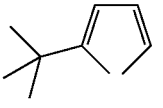 | | — | H | H | T2 | 208-209 |
| 1-456. | Me | | | — | H | Na | T2 | |
| 1-457. | Me | 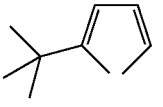 | | — | H | H | T6 | |

TABLE 1-continued

Compounds of the formula (Ia)

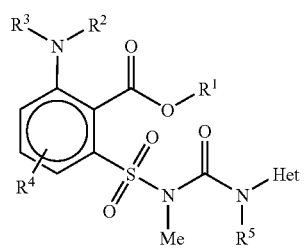
(Ia)

| Ex. No. | R¹ | R² | R³ | R⁴ | R⁵ | M | Het | m.p. |
|---|---|---|---|---|---|---|---|---|
| 1-458. | Me | | *t-Bu-furyl* | — | H | Na | T6 | |
| 1-459. | Me | | *t-Bu-furyl* | — | H | H | T7 | 201-203 |
| 1-460. | Me | | *t-Bu-furyl* | — | H | Na | T7 | |
| 1-461. | Me | | *tetrahydropyranyl* | — | H | H | T1 | |
| 1-462. | Me | | *tetrahydropyranyl* | — | H | Na | T1 | |
| 1-463. | Me | | *tetrahydropyranyl* | — | H | H | T2 | |
| 1-464. | Me | | *tetrahydropyranyl* | — | H | Na | T2 | |
| 1-465. | Me | H | H | 5-Me | H | H | T1 | |
| 1-466. | Me | H | H | 5-Me | H | Na | T1 | |
| 1-467. | Me | H | H | 5-Me | H | H | T2 | |
| 1-468. | Me | H | H | 5-Me | H | Na | T2 | |
| 1-469. | Me | H | H | 5-F | H | H | T1 | |
| 1-470. | Me | H | H | 5-F | H | Na | T1 | |
| 1-471. | Me | H | H | 5-F | H | H | T2 | |
| 1-472. | Me | H | H | 5-F | H | Na | T2 | |
| 1-473. | Me | H | H | 5-Cl | H | H | T1 | |
| 1-474. | Me | H | H | 5-Cl | H | Na | T1 | |
| 1-475. | Me | H | H | 5-Cl | H | H | T2 | |
| 1-476. | Me | H | H | 5-Cl | H | Na | T2 | |
| 1-477. | Me | H | H | 5-OMe | H | H | T1 | |
| 1-478. | Me | H | H | 5-OMe | H | Na | T1 | |
| 1-479. | Me | H | H | 5-OMe | H | H | T2 | |
| 1-480. | Me | H | H | 5-OMe | H | Na | T2 | |
| 1-481. | Me | H | H | 5-NO₂ | H | H | T1 | |
| 1-482. | Me | H | H | 5-NO₂ | H | Na | T1 | |
| 1-483. | Me | H | H | 5-NO₂ | H | H | T2 | |
| 1-484. | Me | H | H | 5-NO₂ | H | Na | T2 | |
| 1-485. | Me | H | H | 6-Me | H | H | T1 | |
| 1-486. | Me | H | H | 6-Me | H | Na | T1 | |

TABLE 1-continued

Compounds of the formula (Ia)

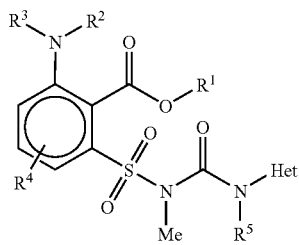

(Ia)

| Ex. No. | R¹ | R² | R³ | R⁴ | R⁵ | M | Het | m.p. |
|---|---|---|---|---|---|---|---|---|
| 1-487. | Me | H | H | 6-Me | H | H | T2 | |
| 1-488. | Me | H | H | 6-Me | H | Na | T2 | |
| 1-489. | Me | H | H | 6-Cl | H | H | T1 | |
| 1-490. | Me | H | H | 6-Cl | H | Na | T1 | |
| 1-491. | Me | H | H | 6-Cl | H | H | T2 | |
| 1-492. | Me | H | H | 6-Cl | H | Na | T2 | |

TABLE 2

Compounds of the formula (Ib)

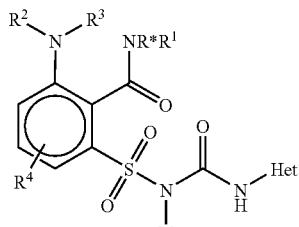

(Ib)

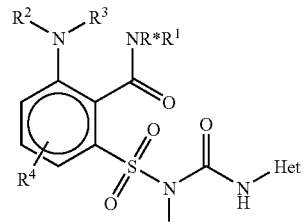

(Ib)

| Ex. No. | R¹ | R* | R² | R³ | R⁴ | M | Het | m.p. |
|---|---|---|---|---|---|---|---|---|
| 2-1. | H | H | H | H | — | H | T1 | |
| 2-2. | H | H | H | H | — | Na | T1 | |
| 2-3. | H | H | H | H | — | H | T2 | |
| 2-4. | H | H | H | H | — | Na | T2 | |
| 2-5. | Me | Me | H | H | — | H | T1 | |
| 2-6. | Me | Me | H | H | — | Na | T1 | |
| 2-7. | Me | Me | H | H | — | H | T2 | |
| 2-8. | Me | Me | H | H | — | Na | T2 | |
| 2-9. | Me | Me | H | H | — | H | T5 | |
| 2-10. | Me | Me | H | H | — | Na | T5 | |
| 2-11. | Me | Me | H | H | — | H | T6 | |
| 2-12. | Me | Me | H | H | — | Na | T6 | |
| 2-13. | Me | Me | H | H | — | H | T7 | |
| 2-14. | Me | Me | H | H | — | Na | T7 | |
| 2-15. | Me | Me | Me | H | — | H | T1 | |
| 2-16. | Me | Me | Me | H | — | Na | T1 | |
| 2-17. | Me | Me | Me | H | — | H | T2 | |
| 2-18. | Me | Me | Me | H | — | Na | T2 | |
| 2-19. | Me | Me | Me | H | — | H | T5 | |
| 2-20. | Me | Me | Me | H | — | Na | T5 | |
| 2-21. | Me | Me | Me | H | — | H | T6 | |
| 2-22. | Me | Me | Me | H | — | Na | T6 | |
| 2-23. | Me | Me | Me | H | — | H | T7 | |
| 2-24. | Me | Me | Me | H | — | Na | T7 | |
| 2-25. | Me | Me | H | H | 5-Me | H | T1 | |
| 2-26. | Me | Me | H | H | 5-Me | Na | T1 | |
| 2-27. | Me | Me | H | H | 5-Me | H | T2 | |
| 2-28. | Me | Me | H | H | 5-Me | Na | T2 | |
| 2-29. | Me | Me | H | H | 5-F | H | T1 | |
| 2-30. | Me | Me | H | H | 5-F | Na | T1 | |
| 2-31. | Me | Me | H | H | 5-F | H | T2 | |
| 2-32. | Me | Me | H | H | 5-F | Na | T2 | |
| 2-33. | Me | Me | H | H | 5-Cl | H | T1 | |
| 2-34. | Me | Me | H | H | 5-Cl | Na | T1 | |
| 2-35. | Me | Me | H | H | 5-OMe | H | T1 | |
| 2-36. | Me | Me | H | H | 5-OMe | Na | T1 | |
| 2-37. | Me | Me | H | H | 5-NO₂ | H | T1 | |
| 2-38. | Me | Me | H | H | 5-NO₂ | Na | T1 | |
| 2-39. | Me | Me | H | H | 6-Me | H | T1 | |
| 2-40. | Me | Me | H | H | 6-Me | Na | T1 | |
| 2-41. | Me | Me | H | H | 6-Cl | H | T1 | |
| 2-42. | Me | Me | H | H | 6-Cl | Na | T1 | |
| 2-43. | Me | Me | Me | H | 5-Me | H | T1 | |
| 2-44. | Me | Me | Me | H | 5-Me | Na | T1 | |
| 2-45. | Me | Me | Me | H | 5-Cl | H | T1 | |
| 2-46. | Me | Me | Me | H | 5-Cl | Na | T1 | |
| 2-47. | Me | Me | Me | H | 5-OMe | H | T1 | |
| 2-48. | Me | Me | Me | H | 5-OMe | Na | T1 | |
| 2-49. | Me | Me | Me | H | 5-NO₂ | H | T1 | |
| 2-50. | Me | Me | Me | H | 5-NO₂ | Na | T1 | |
| 2-51. | Me | Me | Me | H | 6-Me | H | T1 | |
| 2-52. | Me | Me | Me | H | 6-Me | Na | T1 | |
| 2-53. | Me | Me | Me | H | 6-Cl | H | T1 | |
| 2-54. | Me | Me | Me | H | 6-Cl | Na | T1 | |

TABLE 3

Compounds of the formula (VIII)

$$\text{(VIII)}$$

[Structure: benzene ring with $O_2N$-, $COQR^1$, $R^4$, and $SO_2NHC(O)N(R^5)$-Het substituents]

| Ex. No. | $R^1$ | Q | $R^4$ | $R^5$ | Het | m.p. |
|---|---|---|---|---|---|---|
| 3-1. | Me | O | — | H | T1 | |
| 3-2. | Me | O | — | Me | T1 | 161-163 |
| 3-3. | Me | O | — | H | T2 | 212-214 |
| 3-4. | Me | O | — | H | T3 | 218-220 |
| 3-5. | Me | O | — | H | T4 | |
| 3-6. | Me | O | — | H | T5 | |
| 3-7. | Me | O | — | H | T6 | |
| 3-8. | Me | O | — | H | T7 | 211-213 |
| 3-9. | Me | O | — | H | T8 | |
| 3-10. | Me | O | — | H | T9 | |
| 3-11. | Me | O | — | H | T10 | |
| 3-12. | Me | O | — | H | T11 | |
| 3-13. | Me | O | — | H | T12 | |
| 3-14. | Me | O | — | H | T13 | |
| 3-15. | Me | O | — | H | T14 | |
| 3-16. | Me | O | — | H | T15 | |
| 3-17. | Me | O | — | H | T16 | |
| 3-18. | Me | O | — | H | T17 | |
| 3-19. | Me | O | — | H | T18 | |
| 3-20. | Me | O | — | H | T19 | |
| 3-21. | Me | O | — | H | T20 | |
| 3-22. | Et | O | — | H | T1 | 223-225 |
| 3-23. | Et | O | — | H | T2 | 194-196 |
| 3-24. | Et | O | — | H | T6 | |
| 3-25. | Et | O | — | H | T7 | |
| 3-26. | Me | NMe | — | H | T1 | |
| 3-27. | Me | NMe | — | H | T2 | |
| 3-28. | Me | NMe | — | H | T6 | |
| 3-29. | Me | NMe | — | H | T7 | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula: (I), 64 parts by weight of kaolin-containing quartz as inert substance, 10 parts by weight of potassium lignosulfonate and 1 part by weight of sodium oleoylmethyltaurinate as Wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of ethoxylated nonylphenol as the emulsifier.

e) Water-dispersible granules are obtained by mixing
75 parts by weight of a compound of the formula (I),
10 parts by weight of calcium lignosulfonate,
5 parts by weight of sodium lauryl sulfate,
3 parts by weight of polyvinyl alcohol and
7 parts by weight of kaolin
grinding the mixture on a pinned-disk mill and granulating the powder in a fluidized bed by spraying on water as the granulation liquid.

f) Water-dispersible granules are also obtained by homogenizing and precomminuting, on a colloid mill,
25 parts by weight of a compound of the formula (I),
5 parts by weight of sodium 2,2'-dinaphthylmethane-6,6'-disulfonate
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill and atomizing and drying the resulting suspension in a spray tower by means of a single-substance nozzle.

C. Biological Examples

1. Pre-Emergence Effect on Weeds

Seeds or rhizome pieces of monocotyledonous and dicotyledonous weed plants were placed in sandy loam soil in cardboard pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the test results, compounds according to the invention have good herbicidal pre-emergence activity against a broad spectrum of weed grasses and broad-leafed weeds. For example, the compounds of Example Nos. 1-9, 1-11, 1-15, 1-16, 1-17, 1-23, 1-25, 1-26, 1-41, 145, 1-47, 1-55, 1-57, 1-105, 1-129, 1-131, 1-135, 1-153, 1-154, 1-155, 1-159, 1-177, 1-179, 1-189, 1-241, 1-243, 1-247, 1-265, 1-267, 1-271, 1-353, 1-355, 1-359, 1-381, 1-383, 1-387, 1-401, 1-417, 1-425, 1-426, 1-433, 1-435, 1-439, 1-453, 1-455, 1-459 and other compounds of Tables 1 and 2 have very good herbicidal activity against harmful plants such as *Sinapis alba, Chrysanthemum segetum, Avena sativa, Stellaria media, Echinochloa crus-galli, Lolium multiflorum, Setaria* spp., *Abutilon theophrasti, Amaranthus retroflexus* and *Panicum miliaceum*, pre-emergence at an application rate of 0.3 kg and less of active substance per hectar.

2. Post-Emergence Effect on Weeds

Seeds or rhizome pieces of monocotyledonous and dicotyledonous weeds were placed in sandy loam soil in plastic pots, covered with soil and grown in a greenhouse under good growth conditions. Three weeks after sowing, the test plants were treated at the three-leaf stage. The compounds according to the invention which were formulated as wettable powders or emulsion concentrates were sprayed, at various dosages, onto the green parts of the plants at an application rate of 600 to 800 l of water/ha (converted). After the test plants had remained in the greenhouse for about 3 to 4 weeks under ideal growth conditions, the effect of the preparations was scored visually by comparison with untreated controls. The agents according to the invention also have good herbicidal activity post-emergence against a broad spectrum of economically important Weed grasses and broad-loafed weeds. For example, the compounds of Example Nos. 1-9, 1-11, 1-15, 1-16, 1-17, 1-23, 1-25, 1-26, 141, 145, 147, 1-55, 1-57, 1-105, 1-129, 1-131, 1-135, 1-153, 1-154, 1-155, 1-159, 1-177, 1-179, 1-189, 1-241, 1-243, 1-247, 1-265, 1-267, 1-271, 1-353, 1-355, 1-359, 1-381, 1-383, 1-387, 1-401, 1-417, 1-425, 1-426, 1-433, 1-435, 1-439, 1-453, 1-455, 1-459 and other compounds of Tables 1 and 2 have very good herbicidal activity against harmful plants such as *Sinapis alba, Echinochloa crus-galli, Lolium multiflorum, Chrysanthemum segetum, Setaria* spp., *Abutilon theophrasti, Amaranthus retroflexus, Panicum miliaceum* and *Avena sativa* post-emergence at an application rate of 0.3 kg and less of active substance per hectare.

3. Tolerance by Crop Plants

In further greenhouse experiments, seeds of a substantial number of crop plants and weeds were placed in sandy loam soil and covered with soil. Some of the pots were treated immediately as described under Section 1, and the remaining pots were placed in the greenhouse until the plants had developed two to three true leaves and then sprayed with various dosages of the substances of the formula (I) according to the invention, as described under Section 2. Visual scoring four to five weeks after the application and after the plants had been in the greenhouse revealed that compounds according to the invention left dicotyledonous crops such as soya, cotton, oilseed rape, sugar beet or potatoes unharmed even when high dosages of active ingredient were used by the pre- and post-emergence method. Moreover, some substances also spared Gramineae crops such as barley, wheat, rye, sorghum species, corn or rice. Some of the compounds of the formula (I) have high selectivity, and they are therefore suitable for controlling undesirable vegetation in agricultural crops.

The invention claimed is:

1. A compound of the formula (I) or a salt thereof

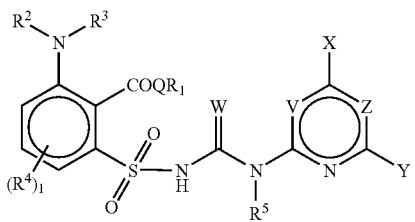

(I)

$R^1$ is H or methyl;

$R^2$ is a group of the formula $R^0\text{-}Q^0\text{-}$, in which $R^0$ is hydrogen or methyl and $Q^0$ is a direct bond;

$R^3$ is hydrogen;

$R^4$ is methyl, fluoro, chloro, methoxy, or $NO_2$;

I is O or 1;

$R^5$ is H;

Q is $NR^*$;

$R^*$ is H or methyl

W is oxygen;

V is N;

X, Y independently of one another are chloro, methyl, or methoxy; and

Z is CH.

2. A compound of the formula (I) or a salt thereof

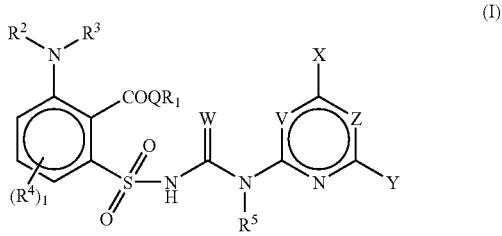

(I)

$R^1$ is methyl or ethyl;

$R^2$ is hydrogen, methyl, ethyl, i-propyl, $CH_2$-i-propyl, $CH_2CH_2CH_2CF_3$, $CH(Me)CH_2CH_3$, c-propyl, or $CH_2Ph$;

$R^3$ is hydrogen, methyl, ethyl or $CH_2$-i-propyl;

I is O;

Q is oxygen;

$R^5$ is hydrogen;

W is oxygen;

V is N;

X, Y independently are methyl, $OCH_3$, chloro, or $OCHF_2$; and

Z is CH.

3. The compound of claim 2, wherein:

X and Y are $OCH_3$.

* * * * *